(12) United States Patent
Cox et al.

(10) Patent No.: US 11,339,419 B2
(45) Date of Patent: May 24, 2022

(54) SCAVENGER PROTEIN(S) FOR IMPROVED PRESERVATION OF ANALYTE DETECTION SENSOR(S) AND METHOD(S) OF USE THEREOF

(71) Applicant: Siemens Healthcare Diagnostics Inc., Tarrytown, NY (US)

(72) Inventors: Janine Cox, Stoughton, MA (US); Christopher Lawrence, Franklin, MA (US); Murli Narayan, Norfolk, MA (US); David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/623,959

(22) PCT Filed: Jul. 30, 2018

(86) PCT No.: PCT/US2018/044333
§ 371 (c)(1),
(2) Date: Dec. 18, 2019

(87) PCT Pub. No.: WO2019/027879
PCT Pub. Date: Feb. 7, 2019

(65) Prior Publication Data
US 2020/0140917 A1    May 7, 2020

Related U.S. Application Data

(60) Provisional application No. 62/539,018, filed on Jul. 31, 2017.

(51) Int. Cl.
*G01N 33/543* (2006.01)
*C12Q 1/26* (2006.01)
(Continued)

(52) U.S. Cl.
CPC .............. *C12Q 1/26* (2013.01); *A61B 5/1473* (2013.01); *B05D 1/36* (2013.01); *G01N 33/5438* (2013.01); *G01N 33/54393* (2013.01)

(58) Field of Classification Search
CPC .......... C12Q 1/26; A61B 5/1473; B05D 1/36; G01N 33/5438; G01N 33/54393
See application file for complete search history.

(56) References Cited

U.S. PATENT DOCUMENTS

| | | |
|---|---|---|
| 7,699,964 B2 | 4/2010 | Feldman et al. |
| 8,523,773 B2 | 9/2013 | Shah et al. |

(Continued)

FOREIGN PATENT DOCUMENTS

| | | |
|---|---|---|
| EP | 0771867 A2 | 5/1997 |
| WO | 2016135136 A1 | 9/2016 |

OTHER PUBLICATIONS

Ariyasu et al. (Bioconjugate Chem. vol. 28, pp. 897-902, published 2017). (Year: 2017).*

(Continued)

*Primary Examiner* — Tracy Vivlemore
*Assistant Examiner* — Nam P Nguyen
(74) *Attorney, Agent, or Firm* — Dunlap Codding, P.C.

(57) ABSTRACT

Composition(s), device(s), kit(s), and method(s) for an improved analyte detection sensor(s) comprising at least one scavenger protein and method(s) of preserving the functioning and functional life of the improved analyte detection sensor(s).

19 Claims, 2 Drawing Sheets

(51) Int. Cl.
   *A61B 5/1473*   (2006.01)
   *B05D 1/36*   (2006.01)

(56) References Cited

U.S. PATENT DOCUMENTS

| | | |
|---|---|---|
| 2006/0275859 A1 | 12/2006 | Kjaer |
| 2007/0105119 A1 | 5/2007 | Gao et al. |
| 2008/0173064 A1 | 7/2008 | Schaffar et al. |
| 2011/0152654 A1 | 6/2011 | Wang et al. |
| 2011/0319734 A1 | 12/2011 | Gottlieb et al. |

OTHER PUBLICATIONS

European Search Report and Written Opinion of European Application No. 18842195.2 dated Jul. 31, 2020.
Tseng et al., "Fabrication of Implantable, Enzyme-Immobilized Glutamate Sensors for the Monitoring of Glutamate Concentration Changes in Vitro and in Vivo", 2014, Molecules, vol. 19, No. 6, pp. 7341-7355.
International Search Report and Written Opinion of International Application No. PCT/US2018/044333 dated Oct. 12, 2018.
Nishiya et al., "Active Site Analysis and Stabilization of Sarcosine Oxidase by the Substitution of Cysteine Residues", Jan. 1995, Applied and Environmental Microbiology, vol. 61, No. 1, pp. 367-370.

\* cited by examiner

SCAVENGER PROTEIN(S) FOR IMPROVED PRESERVATION OF ANALYTE DETECTION SENSOR(S) AND METHOD(S) OF USE THEREOF

CROSS REFERENCE TO RELATED APPLICATIONS

The subject application claims benefit under 35 USC § 119(e) of U.S. provisional Application No. 62/539,018, filed Jul. 31, 2017. The entire contents of the above-referenced patent application are hereby expressly incorporated herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to a composition(s), device(s), kit(s), and method(s) for improving the preservation and functional-life of sensor(s) utilized for analyte(s) detection. More specifically, the presently disclosed and claimed inventive concept(s) relate to at least one scavenger protein(s) that inhibits the inactivation of at least one enzyme(s) present on and/or in sensor(s) utilized for analyte(s) detection.

BACKGROUND

Numerous devices and methods exist for detecting analytes that may be present in a patient's biological fluid sample, including, for instance, a patient's blood, urine, serum, plasma, and/or cerebrospinal fluid sample. Such devices have been proven to be effective in diagnostic assays that detect the presence (or non-presence) as well as the quantity of certain analytes indicative of a patient's health and biological profile, including, but not limited to, analytes and conditions associated with a patient's biological fluid sample, such as, by way of example, a patient's blood and/or urine sample. For instance, blood gas, electrolyte, and/or metabolite analyzers ("BGAs") have been used for years in the medical industry to determine the presence and concentration of certain analytes which may be present in a patient's blood sample. BGAs are routinely used by doctors, scientists, researchers, and medical-care professionals to determine the presence and/or concentrations of certain characteristics and/or analytes present in a patient's blood sample, including, without limitation: (1) blood gases (such as pH (acidity), carbon dioxide (measured as $pCO_2$—partial pressure of carbon dioxide), and/or oxygen (measured as $pO_2$—partial pressure of oxygen)); (2) electrolytes (such as sodium ($Na^+$), potassium ($K^+$), Calcium ($Ca^{2+}$), and/or chloride ($Cl^+$)); (3) metabolites (such as glucose, lactate, biological urea nitrogen (BUN), and/or creatinine); and/or co-oximetry concentration measurements (such as total hemoglobin (tHb), reduced hemoglobin/deoxyhemoglobin (HHb), oxyhemoglobin ($O_2Hb$), saturated oxygen ($sO_2$), carboxyhemoglobin (COHb), methemoglobin (MetHb), fetal hemoglobin (HbF), and/or bilirubin).

BGAs rely on and comprise a sensor array having at least one analyte detection sensor, such as at least one creatinine detection sensor, to accurately detect and/or quantify the analyte(s) of interest present in the patient's biological fluid sample. The consistent and continual functioning of the at least one analyte detection sensor (such as a creatinine detection sensor) is critical to the accurate detection and quantification of the analyte(s) of interest. In addition, improvements that preserve and increase the functional-life of such sensor(s) are highly desired.

To preserve the shelf-life and functionality of analyte detection sensor(s), and, more particularly, creatinine detection sensor(s), at least one biocide may be used in combination with the reagent(s) for the detection of the analyte(s) of interest. However, some of these biocides (such as, by way of example, via the biocide(s) diffusing through a sensor cover membrane) can deactivate critical enzymes necessary for performing the various assays associated with the analyte detection sensor(s), resulting in loss of sensor functionality and/or deterioration of the functional life of the analyte detection sensor(s).

Accordingly, a need exists for new and improved compositions, devices, kits, and methods that preserve or increase the functional life of sensors used to detect and quantify analyte(s) of interest which may be present in a patient's biological fluid sample. Such new and improved compositions, devices, kits, and methods thereby allow, by way of example and not by way of limitation, for: (1) the accurate detection of analyte(s) of interest which may be present in a patient's biological fluid sample; (2) at least the preservation, if not an increase, in the functional life of the analyte detection sensor(s); and (3) cost and time savings due to the re-usability of the of the analyte detection sensor(s). It is to such devices and methods, as well as kits related thereto, that the presently disclosed and claimed inventive concept(s) is directed.

DETAILED DESCRIPTION

Figure 1:
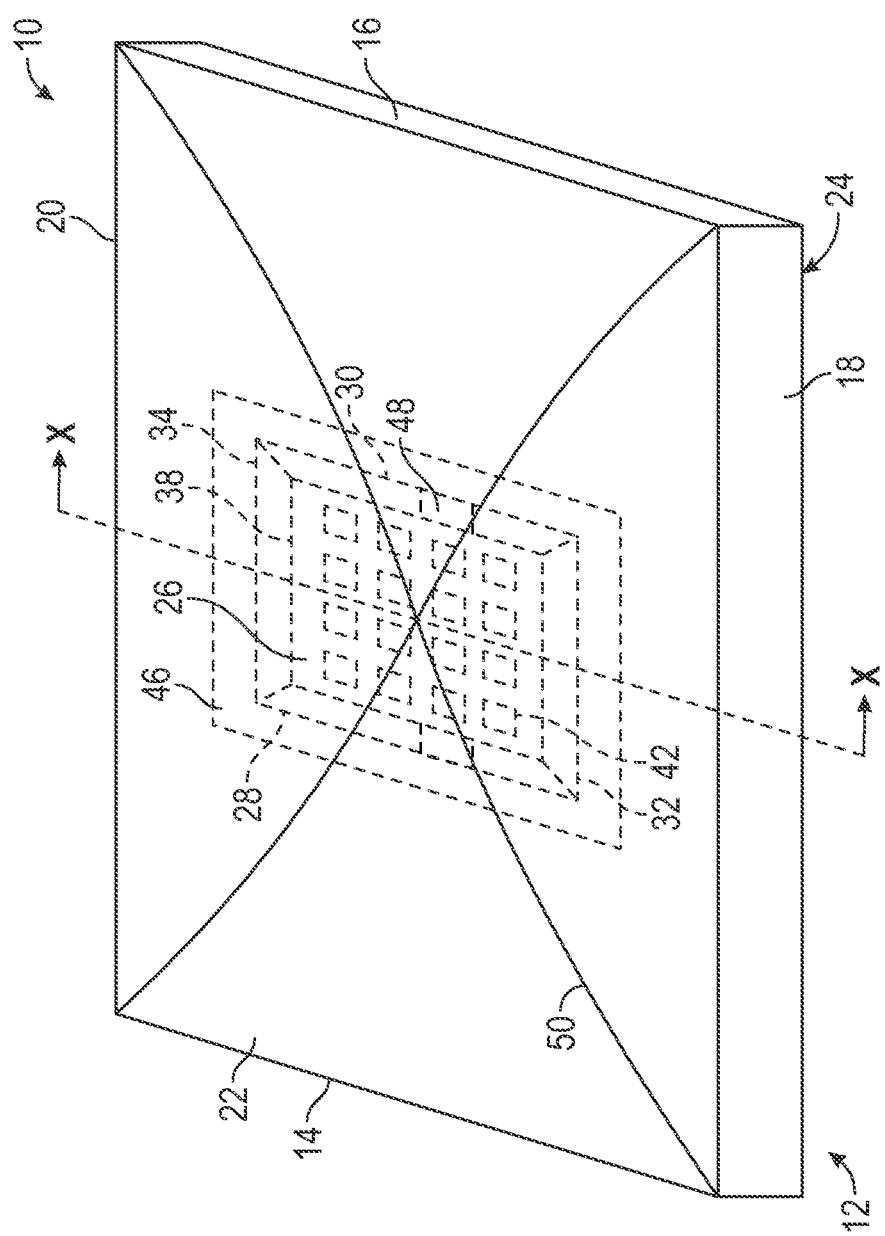
FIG. 1 is a perspective view of a non-limiting embodiment of an improved analyte detection sensor constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or +10%, or +5%, or +1%, or +0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

As used herein, the term "biocide(s)" will be understood to include any substance or combination of substances, including, without limitation, preservatives, antimicrobial agents (including, but not limited to, germicides, antibiotics, antibacterials (including, bactericides), antivirals, antifungals, antiprotozoals, and/or antiparasites), anti-fouling agents, disinfectants, and/or pesticides (including, but not limited to, fungicides, herbicides, insecticides, algicides, molluscicides, miticides, and/or rodenticides) which are used for the control of organisms that are harmful to human and/or animal health and/or that cause damage to natural or manufactured products. Biocides, as used herein, can be of any form, including, without limitation, aqueous (i.e., a fluid) or solid (i.e., a powder). In one non-limiting embodiment, the biocides utilized in accordance with the presently disclosed and/or inventive concept(s) comprise or consist of MIT, Proclin™ 300, and combinations thereof.

The term "biological fluid sample" as used herein will be understood to include any type of biological fluid sample that may be utilized in accordance with the presently disclosed and claimed inventive concept(s). Examples of biological fluid samples that may be utilized include, but are not limited to, whole blood or any portion thereof (i.e., plasma or serum), saliva, sputum, cerebrospinal fluid (CSF), intestinal fluid, intraperitoneal fluid, cystic fluid, sweat, interstitial fluid, tears, mucus, urine, bladder wash, semen, combinations, and the like. In one non-limiting embodiment, the biological fluid sample utilized in accordance with the presently disclosed and/or claimed inventive concept(s) is blood. The volume of the biological fluid sample utilized in accordance with the presently disclosed and claimed inventive concept(s) can be from about 0.1 microliter to about 300 microliters, or from about 0.5 microliter to about 290 microliters, or from about 1 microliter to about 280 microliters, or from about 2 microliters to about 270 microliters, or from about 5 microliters to about 260 microliters, or from about 10 microliters to about 260 microliters, or from about 15 microliters to about 250 microliters, or from about 20 microliters to about 250 microliters, or from about 30 microliters to about 240 microliters, or from about 40 microliters to about 230 microliters, or from about 50 microliters to about 220 microliters, or from about 60 microliters to about 210 microliters, or from about 70 microliters to about 200 microliters, or from about 80 microliters to about 190 microliters, or from about 90 microliters to about 180 microliters, or from about 100 microliters to about 170 microliters, or from about 110 microliters to about 160 microliters, or from about 120 microliters to about 150 microliters, or from about 130 microliters to about 140 microliters. In one non-limiting embodiment, the volume of the fluid sample is in a range of from about 100 microliters to about 200 microliters.

The term "circuitry" as used herein includes, but is not limited to, analog and/or digital components, or one or more suitably programmed processors (e.g., microprocessors) and associated hardware and software or hardwired logic. The term "component" may include hardware, such as but not limited to, a processors (e.g., microprocessor), an application specific integrated circuit (ASIC), field programmable gate array (FPGA), a combination of hardware and software, and/or the like. The term "software" as used herein may include one or more computer readable medium (i.e., computer readable instructions) that when executed by one or more components cause the component to perform a specified function. It should be understood that the algorithms described herein may be stored on one or more non-transient memory. Non-limiting exemplary non-transient memory may include random access memory, read only memory, flash memory, and/or the like. Such non-transient memory may be electrically-based, optically-based, and/or the like.

The term "patient" includes human and veterinary subjects. In certain embodiments, a patient is a mammal. In certain other embodiments, the patient is a human, including, but not limited to, infants, toddlers, children, young adults, adults, and elderly human populations. "Mammal" for purposes of treatment refers to any animal classified as a mammal, including human, domestic and farm animals, nonhuman primates, and zoo, sports, or pet animals, such as dogs, horses, cats, cows, etc.

The terms "peptide", "polypeptide" and "protein" are used herein to refer to a polymer of amino acid residues. The term "polypeptide" as used herein is a generic term to refer to native protein, protein fragments, or analogs of a polypeptide sequence. Hence, native protein, protein fragments, and analogs are species of the polypeptide genus. In one non-limiting embodiment of the presently disclosed and/or claimed inventive concept(s), the peptide(s), polypeptide(s), protein(s), and/or polymer(s) comprise thiol(s) and/or thiol-containing constituents.

Turning now to particular embodiments, the presently disclosed and claimed inventive concept(s) relate to a composition(s), device(s), kit(s), and method(s) for preserving and/or improving the functional life and performance of analyte detection sensor(s) of blood gas, electrolyte, and/or metabolite instrumentation. While a patient's biological fluid sample is primarily discussed herein in the context of a patient's blood sample, it should be readily understood by a person having ordinary skill in the art that the presently disclosed and/or claimed inventive concepts have applications to all types of a patient's biological fluid sample. More specifically, the presently disclosed and claimed inventive concept(s) relate to composition(s), device(s), kit(s), and method(s) for improving the functional life and performance of at least one creatinine sensor(s) of a blood gas, electrolyte, and/or metabolite instrumentation via the use of a scavenger protein layer comprising at least one scavenger protein, as well as kits and methods of use related thereto.

Biocides are often used to preserve analyte detection sensor(s) of a sensor array present in a blood gas, electrolyte, and/or metabolite instrument. However, when such analyte detection sensor(s) are creatinine detection sensor(s), these biocides inactivate some or all of the enzymes present on and/or in the creatinine sensor(s). In the context of creatinine sensors, such sensors rely on enzymes containing free sulfhydryl groups (—SH) for the proper and continuous functioning of the sensors. Such free sulfhydryl groups chemically react with the biocide(s) that result in the inactivation of the creatinine sensor's(s') enzymes, thereby resulting in decreased (or total loss) of functional utility and/or functional life of the creatinine sensor(s). In fact, as shown in more detail below in the tables, such inactivation can occur (in the absence of at least one scavenger protein) as soon as four (4) days after exposure of the creatinine sensor(s) with such biocide(s).

Non-limiting examples of enzymes utilized in accordance with the presently disclosed and/or claimed inventive concept(s) include, without limitation, creatininase, creatinase, and sarcosine oxidase-however, it should be readily understood by a person having ordinary skill in the art that the presently disclosed and/or claimed inventive concept(s) are not limited to these specific enzymes and that any enzyme(s) applicable to creatinine-based and/or other analyte detection sensors can be utilized in accordance with the scope of the presently disclosed and/or claimed inventive concept(s).

Non-limiting examples of biocides utilized in accordance with the presently disclosed and/or claimed inventive concept(s) include, without limitation, methylisothiazolinone ("MIT") and, for instance, Proclin™ 300, which comprises a combination of 5-chloro-2-methyl-4-isothiazolin-3-one ("CMIT"), MIT, proprietary glycol, and modified alkyl carboxylate, and which is commercially offered for sale by Sigma-Aldrich Corporation and/or the Dow Chemical Company-however, it should be readily apparent to a person having ordinary skill in the art that the presently disclosed and/or claimed inventive concept(s) are not limited to these specific biocides and that any biocide(s) applicable to creatinine-based and/or other analyte detection sensors can be utilized in accordance with the scope of the presently disclosed and/or claimed inventive concept(s).

The scavenger protein(s) utilized in accordance with the presently disclosed and/or claimed inventive concept(s) can be any protein(s) capable of complexing and/or associating with the biocides, including, without limitation, proteins having free thiol/sulfhydryl functional groups and/or sulfide/disulfide bonds (such as monothiols and/or polythiols) such as, by way of example only, bovine serum albumin ("BSA"), thioredoxin, urease, glutathione, cadystin, phytochelatin, homoglutathione, homophytochelatin, desGly peptide, desglycine phytochelatin, hydroxymethyl-glutathione, hydroxymethyl-phytochelatin, and/or combinations thereof. In one non-limiting embodiment of the presently disclosed and/or claimed inventive concept(s), the scavenger protein comprises or consists of BSA, which itself comprises one sulfhydryl functional group and seventeen (17) disulfide bonds. Alternatively or in addition to, the reduced form of BSA may be used as a scavenger protein in accordance with the presently disclosed and/or claimed inventive concept(s). The reduced form of BSA is formed by exposing the BSA protein to a reducing agent(s), such as, by way of example only, [laundry list of reducing agents]. The reduced form of BSA rearranges the disulfide bonds of the BSA to thereby increase the number of free thiol/sulfhydryl groups available for reacting with the biocide(s). In such non-limiting embodiments, BSA (and/or reduced BSA) is a desired scavenger protein given its chemical makeup which allows for it to easily associate with biocides, but also due to it being inexpensive, which allows for substantial cost savings. In addition, BSA can be easily integrated into current and/or next generation blood gas, electrolyte, and/or metabolite instruments without substantively altering the existing reagents, protocols, or structures of such instruments.

One aspect of the presently disclosed and/or claimed inventive concept(s) embodies an improved analyte detection sensor array. The improved analyte detection sensor array comprises at least one analyte detection sensor which is in fluid communication with a biocide preservation fluid. In one-non-limiting embodiment, the improved analyte detection sensor array is well adapted for incorporation and use in blood gas, electrolyte, and/or metabolite instrumentation. The improved analyte detection sensor array may, in one non-limiting embodiment, be contained within a housing, for instance, a cartridge for use in a blood gas, electrolyte, and/or metabolite instrument. The improved analyte detection sensor array may comprise any number of analyte detection sensors in order to accomplish the presently disclosed and/or claimed inventive concept(s). For instance, by way of example only, the improved analyte detection sensor array may comprise 1, 2, 3, 4, 5, 6, 7, 8, 9, 10, 15, 20, 25, 30, 35, 40, 45, 50, 55, 60, 65, 70, 75, 80, 85, 90, 95, or greater than or equal to 100 analyte detection sensors.

Referring now to the Figures, and, in particular FIG. 1, shown therein is a non-limiting embodiment of the at least one analyte detection sensor 10 constructed in accordance with the presently disclosed and/or claimed inventive concept(s). In such non-limiting embodiment, the at least one analyte detection sensor 10 comprises a substrate 12, an enzyme layer 38, a scavenger protein layer 46, at least one electrode 48, and a sensor membrane cover 50.

The substrate 12 comprises a first side 14, a second side 16, a third side 18, a fourth side 20, a top surface 22, and a bottom surface 24. While shown in FIG. 1 as being substantially rectangular in shape, it should be readily understood to a person having ordinary skill in the art that the substrate 12 can be any shape conducive for accomplishing the presently disclosed and/or claimed inventive concept(s). Such shapes include, but are not limited to, a circle, triangle, square, diamond, pentagon, hexagon, heptagon, octagon, nonagon, decagon, rhombus, trapezoid, rhombus, and parallelogram. The substrate 12 can be constructed of any inert material(s) that accomplish the presently disclosed and/or claimed inventive concept(s), including, without limitation, ceramic(s), nitrocellulose, cellulose acetate, polyethylene terephthalate, polycarbonate, polystyrene, and combinations thereof.

In one non-limiting embodiment, and as shown in FIG. 1, the substrate 12 further comprises a reaction cavity 26. In such embodiment (and as further shown in FIG. 2), the reaction cavity 26 is located between the top surface 22 and bottom surface 24 of the substrate 12. The reaction cavity 26 comprises a first side 28, a second side 30, a third side 32, and a fourth side 34, and an opening (not numbered) located near the top surface 22 of the substrate 12, the opening being defined by the first side 28, the second side 30, the third side 32, and the fourth side 34 of the reaction cavity 26. As shown in FIG. 1, the first side 28 of the reaction cavity 26 is substantially parallel to the first side 14 of the substrate 12. Similarly, the second side 30, the third side 32, and the fourth side of the reaction cavity 28 are each substantially parallel to the second side 16, the third side 18, and fourth side 20 of the substrate, respectively. While shown in FIG. 1 as comprising a reaction cavity 26, it should be readily understood to a person having ordinary skill in the art that the substrate 12 need not comprise the reaction cavity 26 to accomplish the presently disclosed and/or claimed inventive concept(s). For instance, as further described herein, the enzyme layer 38, the scavenger protein layer 46, the at least one electrode 48, and the sensor membrane cover 50 may all be located on or substantially on the top surface 22 of the substrate 12. In addition, it should be readily understood to a person having ordinary skill in the art that the substrate 12 may comprise more than one reaction cavity 26 to accomplish the presently disclosed and/or claimed inventive concept(s). For instance, by way of example only, the substrate 12 may comprise 2, 3, 4, 5, 6, 7, 8, 9, 10, 15, 20, 25, 30, 35, 40, 45, 50, 55, 60, 65, 70, 75, 80, 85, 90, 95, or greater than or equal to 100 reaction cavities.

The at least one analyte detection sensor 10 (for instance, by way of example only, at least one creatinine detection sensor) comprises an enzyme layer 38 that comprises at least one enzyme 42. While shown in FIG. 1 as comprising a single enzyme layer 38, it should be readily understood to a person having ordinary skill in the art that the at least one analyte detection sensor 10 may comprise more than one enzyme layer 38. For instance, by way of example only, the at least one analyte detection sensor 10 may comprise 2, 3, 4, 5, 6, 7, 8, 9, 10, 15, 20, 25, 30, 35, 40, 45, 50, 55, 60, 65, 70, 75, 80, 85, 90, 95, or greater than or equal to 100 enzyme layers. In one non-limiting embodiment, the at least one enzyme 42 comprises or consists of creatininase, creatinase, sarcosine oxidase, and/or combinations thereof. The at least one enzyme 42 functions by associating with the analyte of interest (i.e., creatinine) to provide for accurate detection and concentration of the analyte of interest which may be present in a patient's biological fluid sample, which, in one non-limiting embodiment, is a patient's blood sample. As shown in FIG. 1, the enzyme layer 38 comprises at least one immobilized enzyme(s) 42, the enzyme layer 38 being substantially disposed in the reaction cavity 26. However, it should be readily understood to a person having ordinary skill in the art that the enzyme layer 38 may be disposed on the at least one electrode 48 (discussed further hereinbelow), the at least one electrode being located in the reaction cavity 26 or otherwise imbedded within the top surface 22 of the substrate 12.

The at least one analyte detection sensor 10 further comprises a scavenger protein layer 46 that comprises at least one scavenger protein (not shown). While shown in FIG. 1 as comprising a single scavenger protein layer 46, it should be understood by a person having ordinary skill in the art that the at least one analyte detection sensor 10 may comprise more than one scavenger protein layer 46. For instance, by way of example only, the at least one analyte detection sensor 10 may comprise 2, 3, 4, 5, 6, 7, 8, 9, 10, 15, 20, 25, 30, 35, 40, 45, 50, 55, 60, 65, 70, 75, 80, 85, 90, 95, or greater than or equal to 100 scavenger protein layers. In one non-limiting embodiment, the at least one scavenger protein of the scavenger protein layer 46 comprises at least one free sulfhydryl functional group; however, a person having ordinary skill in the art should readily understood by a person having ordinary skill in the art that the at least one scavenger protein can contain any number of sulfhydryl functional groups (and/or sulfide and/or disulfide bonds) that accomplishes the presently disclosed and/or claimed inventive concept(s). For instance, by way of example and not by way of limitation, the scavenger protein(s) may comprise 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or greater than or equal to 100 sulfhydryl functional groups. In one non-limiting embodiment, the at least one scavenger protein comprises from about 1 to about 20 free sulfhydryl functional groups. Similarly, the scavenger protein(s) may comprise 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or greater than or equal to 100 sulfide and/or disulfide bonds. Non-limiting examples of scavenger proteins utilized in accordance with the presently disclosed and/or claimed inventive concepts include, but are not limited to, BSA, thioredoxin, urease, glutathione, cadystin, phytochelatin, homoglutathione, homophytochelatin, desGly peptide, desglycine phytochelatin, hydroxymethyl-glutathione, hydroxymethyl-phytochelatin, and/or combinations thereof. In one non-limiting embodiment, the scavenger protein comprises BSA.

As shown in FIG. 1 (and further detailed in FIG. 2), the scavenger protein layer 46 is disposed above the enzyme layer 38, such that the scavenger protein layer 46 shields and/or protects the enzyme layer 38 from a biocide (discussed in further detail herein below). Accordingly, the shielding and/or protection of the enzyme layer 38 by the scavenger protein layer 46 mitigates and/or eliminates the inactivation of the at least one enzyme 42 of the enzyme layer 38 by the biocide. In one non-limiting embodiment, the scavenger protein layer 46 comprises a dry film-like layer that, when exposed to a buffer and/or wash solution, reconstitutes into an aqueous or semi-aqueous layer that shields the enzyme layer 38 from the biocide(s). The shielding and/or protection by the protein scavenger layer thereby increases the functional life of the improved analyte detection sensor 10 by preventing the inactivation of the enzyme layer 38 by the biocide. The scavenger protein layer 46 may comprise: (1) an aqueous solution of the at least one scavenger protein that is located above and in fluid communication with the enzyme layer 38; (2) scavenger protein(s) that are immobilized on or within the enzyme layer 38 (such as, by way of example only, immobilized scavenger protein(s) associated with the at least one enzyme 42 that is/are cross-linked with one another within the enzyme layer 38); and/or (3) the at least one scavenger protein can be incorporated via polymerization into the sensor membrane cover 50.

The concentration of the at least one scavenger protein of the scavenger protein layer 46 (for instance, by way of example only, the BSA scavenger protein comprising an aqueous solution above the enzyme layer 38) can be from about 0.1 milligram per milliliter ("mg/mL") to about 200 mg/mL, or from about 0.5 mg/mL to about 195 mg/mL, or from about 1 mg/mL to about 190 mg/mL or from about 5 mg/mL to about 185 mg/mL, or from about 10 mg/mL to about 180 mg/mL, or from about 15 mg/mL to about 180 mg/mL, or from about 20 mg/mL to about 175 mg/mL, or from about 25 mg/mL to about 170 mg/mL, or from about 30 mg/mL to about 165 mg/mL, or from about 35 mg/mL to about 160 mg/mL, or from about 40 mg/mL to about 155 mg/mL, or from about 45 mg/mL to about 150 mg/mL, or from about 50 mg/mL to about 145 mg/mL, or from about 55 mg/mL to about 140 mg/mL, or from about 60 mg/mL to about 135 mg/mL, or from about 65 mg/mL to about 130 mg/mL, or from about 70 mg/mL to about 125 mg/mL, or from about 75 mg/mL to about 120 mg/mL, or from about 80 mg/mL to about 115 mg/mL, or from about 85 mg/mL to about 110 mg/mL, or from about 90 mg/mL to about 105 mg/mL, or from about 95 mg/mL to about 100 mg/mL, or less than or equal to about 100 mg/mL. In one non-limiting embodiment, the concentration of the at least one protein scavenger (for instance, by way of example only, the BSA protein scavenger) is from about 0.1 mg/mL to about 50 mg/mL.

Figure 2:
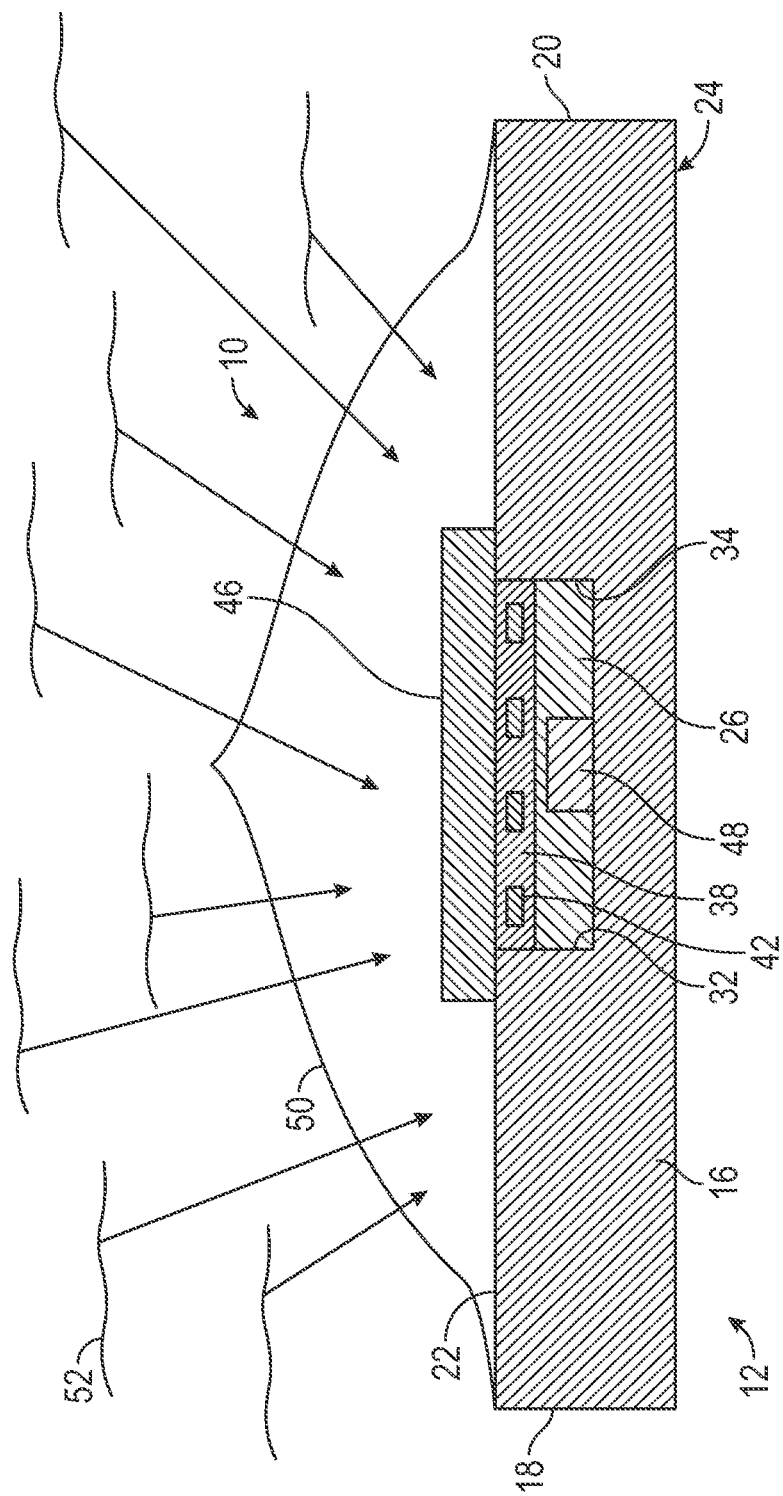
FIG. 2 is a cross-sectional view of the improved analyte detection sensor of FIG. 1 as viewed from the cross-sectional line x of FIG. 1 in which the improved analyte detection sensor is in fluid communication with at least one aqueous biocide.

The improved analyte detection sensor(s) further comprise at least one electrode 48 for the detection of at least one analyte of interest present in a patient's fluid sample. In one non-limiting embodiment and as shown in FIGS. 1 and 2, the at least one electrode 48 rests below the enzyme layer 38 within the reaction cavity 26 of the substrate 12. In one non-limiting embodiment, the at least one electrode 48 comprises an amperometric electrode system that comprises at least one working electrode, at least one counter electrode, and at least one reference electrode in which the enzyme layer is disposed on or substantially on the at least one working electrode. When an analyte of interest (for instance, creatinine) comes into contact with the enzyme layer 38 (which, in one non-limiting embodiment, comprises at least one enzyme 42 including, without limitation, creatininase, creatinase, sarcosine oxidase, and/or combinations thereof), reaction product(s), such as ions and/or detection molecules (such as, by way of example only, hydrogen peroxide) are generated from the reaction of the analyte of interest and the at least one enzyme 42 of the enzyme layer 38. Such reaction product(s), when in contact with the at least one electrode 48, generate an electric current or changes in an electric current (typically measured in amperes or nano amperes) which are readily detected and measured by the at least one electrode 48. The current generated by the at least one electrode 48 is directly proportional to the concentration of the particular analyte of interest being tested, which, in one non-limiting embodiment, is creatinine. A non-limiting embodiment of the at least one electrode 48 that may be utilized in accordance with the presently disclosed and/or claimed inventive concept(s) includes a bare metal electrode. However, other electrode(s) that are capable of functioning as described or otherwise contemplated herein are well known in the art and encompassed by the presently disclosed and/or claimed inventive concept(s), and, therefore, no further discussion thereof is deemed necessary.

The improved analyte detection sensor 10 further comprises at least one sensor membrane cover 50 that, in one non-limiting embodiment, substantially covers the top surface 22 of the substrate 12 (as well as the entirety of the reaction cavity 26, the enzyme layer 38, the scavenger protein layer 46, and the at least one electrode 48) of the improved analyte detection sensor 10. However, it should be readily understood to a person having ordinary skill in the art that the at least one sensor membrane cover 50 need not substantially cover the entirety of the top surface 22 of the substrate 12 to accomplish the presently disclosed and/or claimed inventive concept(s). For instance, when the improved analyte detection sensor array comprises more than one analyte detection sensor, each of the analyte detection sensors may be covered by a separate sensor membrane cover(s), which may be constructed of the same or different material(s). In addition, rather than substantially covering the top surface 22 of the substrate 12, the at least one sensor membrane cover 50 may cover the at least one scavenger protein layer 46 rather than the entirety of the top surface 22 of the substrate 12.

The at least one sensor membrane cover 50 can be constructed of any permeable material capable of accomplishing the presently disclosed and/or claimed inventive concept(s), including, but not limited to, cellulosic and/or polymeric (such as, by way of example, polyurethane) materials, and/or combinations thereof. The at least one sensor cover membrane 50 acts as a permeable cover for the analyte detection sensor 10 in which the biocide (as shown in FIG. 2) diffuses through the at least one sensor cover membrane 50 such that the biocide is in fluid communication with the scavenger protein layer 46 (as well as the scavenger protein(s) comprising the scavenger protein layer 46).

Referring now to FIG. 2, shown therein is a cross-sectional view of the improved analyte detection sensor 10 of FIG. 1, wherein the analyte detection sensor 10 is in fluid communication with at least one aqueous biocide 52. As previously discussed herein, the at least one aqueous biocide 52 functions as a preservative of the at least one improved analyte detection sensor 10 of the sensor array to thereby increase a functional life of the improved analyte detection sensor 10. The functional life of the improved analyte detection sensor 10 is preferably equal to or greater than 14 days or greater than or equal to 28 days. However, when the at least one analyte detection sensor 10 comprises a creatinine detection sensor, certain biocides 52, such as, by way of example only, MIT and Proclin™ 300, can inactivate the at least one enzyme 42 of the enzyme layer 38 due to the chemical interactions between the sulfhydryl functional groups of the enzyme(s) 42 and the biocide(s) 52. In some instances, the inactivation of the enzyme(s) 42 of the creatinine analyte detection sensor 10 occurs in as short as 1-4 days after exposure to the biocide(s) 52. Accordingly, the presently disclosed and/or claimed inventive concept(s) utilize a scavenger protein layer 46 comprising at least one scavenger protein (not shown) for decreasing and/or eliminating the chemical interactions between the enzyme(s) 42 of the enzyme layer 38 of the creatinine analyte detection sensor(s) 10 and the biocide(s) 52 to thereby increase the functional life of the creatinine analyte detection sensor(s) 10.

When the at least one aqueous biocide 52 and the at least one scavenger protein are in fluid communication with each other (via diffusion of the at least one aqueous biocide 52 through the sensor membrane cover 50—as represented by the downward arrows in FIG. 2), the at least one aqueous biocide 52 complexes and/or associates with the sulfhydryl functional group(s) (and/or the sulfide and/or disulfide bond(s)) of the at least one scavenger protein (for instance, the at least one scavenger protein of the scavenger protein layer 46). As a result of this association, detrimental effect(s) resulting from the biocide's(s') 52 association with the at least one enzyme 42 of the enzyme layer 38 of the at least one analyte detection sensor(s) 10 (for instance, the at least one creatinine sensor) is/are mitigated, if not eliminated in its/their entirety. Accordingly, the preservative effects of the at least one biocide 52 is maintained (i.e., for non-creatinine detection sensor(s)), while the detrimental effects resulting from the biocide's(s') 52 association with the sulfhydryl functional groups present in the at least one enzyme 42 of the enzyme layer 38 of the analyte detection sensor 10 are mitigated (or even eliminated), thereby improving the functional life of the analyte detection sensor(s) 10, including, without limitation, the at least one creatinine detection sensor.

The concentration of the at least one aqueous biocide 52 can be any concentration(s) capable of accomplishing the presently disclosed and/or claimed inventive concept(s). For instance, when the aqueous biocide 52 comprises Proclin™ 300, the concentration of Proclin™ 300 in the aqueous biocide 52 can be from about 0.1% to about 2.0%, or from about 0.2% to about 1.9%, or from about 0.3% to about 1.8%, or from about 0.4% to about 1.7%, or from about 0.5% to about 1.6%, or from about 0.6% to about 1.5%, or from about 0.7% to about 1.4%. In one non-limiting embodiment, the concentration of Proclin™ 300 in the aqueous biocide 52 is from about 0.1% to about 2.0%. Similarly, when, for instance, the aqueous biocide 52 comprises MIT, the concentration of MIT in the biocide 52 can be from about 1 to about 200 parts per million ("ppm"), or from about 2 ppm to about 190 ppm, or from about 5 ppm to about 185 ppm, or from about 10 ppm to about 180 ppm, or from about 15 ppm to about 175 ppm, or from about 20 ppm to about 170 ppm, or from about 25 ppm to about 165 ppm, or from about 30 ppm to about 160 ppm, or from about 35 ppm to about 155 ppm, or from about 40 ppm to about 150 ppm, or from about 45 ppm to about 145 ppm, or from about 50 ppm to about 140 ppm or from about 55 to about 135 ppm, or from about 60 ppm to about 130 ppm, or from about 65 ppm to about 125 ppm, or from about 70 ppm to about 120 ppm, or from about 75 ppm to about 115 ppm, or from about 80 ppm to about 110 ppm, or from about 85 ppm to about 105 ppm, or from about 90 ppm to about 100 ppm. In one non-limiting embodiment, the concentration of MIT in the biocide 52 is in a range of from about 1 ppm to about 150 ppm.

One aspect of the presently disclosed and/or claimed inventive concept(s) embodies a method for preventing the inactivation of at least one analyte detection sensor 10 (for instance, by way of example only, a creatinine detection sensor(s) and as previously described herein with respect to the presently disclosed and/or claimed inventive concept(s)) for use within blood gas, electrolyte, and/or metabolite instrumentation. The method comprises the step of introducing at least one aqueous biocide 52 (such as, by way of example only, MIT, Proclin™ 300, and/or combinations thereof), such that the at least one aqueous biocide 52 is in fluid communication with at least one analyte detection sensor 10. The at least one biocide 52, via diffusion through a sensor membrane cover 50, thereafter comes into fluid communication with a scavenger protein layer 46 comprising at least one scavenger protein having at least one free sulfhydryl functional group (such as, by way of example, BSA, thioredoxin, urease, and/or combinations thereof). As a result of this fluid communication between the at least one biocide 52 and the scavenger protein layer 46, the at least one aqueous biocide 52 complexes and/or associates with the at least one free sulfhydryl functional group of the at least one scavenger protein of the scavenger protein layer 46 thereby forming a complexed biocide.

Following the formation of the complexed biocide, the complexed biocide is brought into fluid communication with the at least one analyte detection sensor 10 (for instance, the creatinine sensor). Via this contact, the complexed biocide (due to the association between the at least one free sulfhydryl functional group of the at least one scavenger protein of the scavenger protein layer 46 and the at least one aqueous biocide 52) prevents the inactivation of at least one enzyme 42 comprising the enzyme layer 38 of the analyte detection sensor(s) 10. Accordingly, the at least one enzyme 42 of the enzyme layer 38 is not (or is at least mitigated from being) inactivated by the aqueous biocide 52 as a result of the association, which thereby extends the functional life of the at least one analyte detection sensor 10.

Examples of Utilizing BSA as a Scavenger Protein of MIT and Proclin™ 300 Biocides for Preservation of Sarcosine Oxidase and Creatininase Enzymatic Activities of a Creatinine Sensor The tables below represent varying conditions utilized to test the effectiveness of BSA as a viable scavenger protein of aqueous MIT and Proclin™ 300 biocides, as well as BSA's preservation effects on sarcosine oxidase and creatininase enzyme activities-enzymes utilized in accordance with the creatinine sensor(s) of the presently disclosed and/or claimed inventive concept(s).

Tables 1-4 depict aqueous solutions comprising varying concentrations of BSA (at concentrations of 0 mg/mL, 5 mg/mL, 25 mg/mL, and 50 mg/mL), varying concentrations of MIT (at concentrations of 50 parts per million and 100 parts per million) or Proclin™ 300 (at concentrations of 0.7% and 1.4%) biocides over a particular time period (measurements were taken at days 0, 4, and 14 after exposure of the enzyme(s) to the aqueous solutions) and the associated enzyme absorbance measurements for sarcosine oxidase (commercially offered for sale by BBI Solutions and Toyobo). Absorbance measurements of the sarcosine oxidase enzyme(s) were taken via spectrophotometer for each aqueous solution (represented as columns 1-5 in Tables 1-4—column 6 is a blank), the absorbance being directly proportional to the enzyme activity being measured-which for Tables 1-4 is sarcosine oxidase enzyme activity. Accordingly, the higher the absorbance measurement, the higher the enzyme activity of sarcosine oxidase. Columns 7-11 represent five replicate readings in which the aqueous solution only contains BSA (i.e., there is no biocide(s) present in the aqueous solution). In addition, the mean values, standard deviations, and coefficients of variation are also presented for the enzyme activity/absorbance of each aqueous solution. All measurements were taken at 37° C.

As depicted below in Table 1, sarcosine oxidase (commercially offered for sale by BBI Solutions) enzyme activity is measured against various concentrations of MIT (biocide) and BSA (scavenger protein) over a period of 14 days (with absorbance measurements taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the MIT biocide. As can be clearly seen in Table 1, at days 4 and 14, the aqueous solutions (columns 1-5) comprising 5 mg/mL, 25 mg/mL, and 50 mg/mL concentrations of BSA show increased absorbance of the sarcosine oxidase enzyme (as compared to the samples containing 0 mg/mL of BSA). Such absorbance readings confirm the preservative effect of the BSA scavenger protein on the sarcosine oxidase enzyme activity in the presence of MIT biocide. In addition, solutions 7-11, which only contain BSA and no MIT biocide, also show increased (or at least maintained) sarcosine oxidase absorbance at days 4 and 14, which further illustrates BSA's preservative effect on sarcosine oxidase enzyme activity.

TABLE 1

BBI Solutions Sarcosine Oxidase Enzyme Absorbance with BSA and MIT

| Day 0 | BSA | 1 | 2 | 3 | 4 | 5 | 6 | MEAN | Stdev | CV | 7 |
|---|---|---|---|---|---|---|---|---|---|---|---|
| 100 ppm MIT | 0 mg/mL | 1.446 | 1.428 | 1.422 | 1.427 | 1.423 | 0.039 | 1.39 | 0.01 | 0.70 | 1.452 |
| | 5 mg/mL | 1.41 | 1.418 | 1.423 | 1.42 | 1.425 | 0.039 | 1.38 | 0.01 | 0.42 | 1.425 |
| | 25 mg/mL | 1.447 | 1.459 | 1.456 | 1.449 | 1.468 | 0.055 | 1.41 | 0.01 | 0.59 | 1.436 |
| | 50 mg/mL | 1.396 | 1.419 | 1.45 | 1.414 | 1.413 | 0.04 | 1.38 | 0.02 | 1.43 | 1.403 |
| 50 ppm MIT | 0 mg/mL | 1.463 | 1.459 | 1.507 | 1.474 | 1.477 | 0.039 | 1.43 | 0.02 | 1.31 | 1.428 |
| | 5 mg/mL | 1.484 | 1.435 | 1.486 | 1.455 | 1.454 | 0.039 | 1.42 | 0.02 | 1.53 | 1.428 |
| | 25 mg/mL | 1.385 | 1.39 | 1.401 | 1.423 | 1.433 | 0.039 | 1.37 | 0.02 | 1.53 | 1.434 |
| | 50 mg/mL | 1.445 | 1.468 | 1.458 | 1.406 | 1.484 | 0.039 | 1.41 | 0.03 | 2.09 | 1.454 |
| | | | | | | | 0.041125 | | | | |

| Day 0 | BSA | 8 | 9 | 10 | 11 | 12 | MEAN | Stdev | CV | % Bias |
|---|---|---|---|---|---|---|---|---|---|---|
| 100 ppm MIT | 0 mg/mL | 1.409 | 1.405 | 1.411 | 1.405 | 0.045 | 1.37 | 0.02 | 1.46 | 1.3 |
| | 5 mg/mL | 1.439 | 1.414 | 1.437 | 1.422 | 0.046 | 1.38 | 0.01 | 0.76 | −0.3 |
| | 25 mg/mL | 1.43 | 1.428 | 1.409 | 1.458 | 0.045 | 1.39 | 0.02 | 1.27 | 2.0 |
| | 50 mg/mL | 1.406 | 1.388 | 1.393 | 1.395 | 0.046 | 1.35 | 0.01 | 0.55 | 1.9 |
| 50 ppm MIT | 0 mg/mL | 1.416 | 1.424 | 1.438 | 1.433 | 0.045 | 1.38 | 0.01 | 0.61 | 3.8 |
| | 5 mg/mL | 1.432 | 1.435 | 1.451 | 1.43 | 0.046 | 1.39 | 0.01 | 0.66 | 2.3 |
| | 25 mg/mL | 1.435 | 1.421 | 1.396 | 1.399 | 0.046 | 1.37 | 0.02 | 1.36 | −0.5 |
| | 50 mg/mL | 1.428 | 1.464 | 1.467 | 1.474 | 0.045 | 1.41 | 0.02 | 1.27 | −0.1 |
| | | | | | | 0.0455 | | | | |

| Day 4 | | 1 | 2 | 3 | 4 | 5 | 6 | MEAN | Stdev | CV | 7 |
|---|---|---|---|---|---|---|---|---|---|---|---|
| 100 ppm | 0 mg/mL | 1.38 | 1.379 | 1.384 | 1.384 | 1.353 | 0.032 | 1.35 | 0.01 | 0.97 | 1.316 |
| | 5 mg/mL | 1.404 | 1.416 | 1.435 | 1.404 | 1.42 | 0.03 | 1.38 | 0.01 | 0.93 | 1.342 |

TABLE 1-continued

BBI Solutions Sarcosine Oxidase Enzyme Absorbance with BSA and MIT

| | | | | | | | | | | | |
|---|---|---|---|---|---|---|---|---|---|---|---|
| MIT | 25 mg/mL | 1.42 | 1.392 | 1.415 | 1.383 | 1.4 | 0.031 | 1.37 | 0.02 | 1.13 | 1.371 |
| | 50 mg/mL | 1.397 | 1.396 | 1.413 | 1.425 | 1.412 | 0.031 | 1.38 | 0.01 | 0.88 | 1.386 |
| 50 | 0 mg/mL | 1.388 | 1.397 | 1.401 | 1.346 | 1.368 | 0.031 | 1.35 | 0.02 | 1.70 | 1.357 |
| ppm | 5 mg/mL | 1.47 | 1.47 | 1.446 | 1.456 | 1.467 | 0.031 | 1.43 | 0.01 | 0.74 | 1.448 |
| MIT | 25 mg/mL | 1.446 | 1.431 | 1.432 | 1.448 | 1.434 | 0.031 | 1.41 | 0.01 | 0.58 | 1.419 |
| | 50 mg/mL | 1.429 | 1.415 | 1.37 | 1.398 | 1.381 | 0.031 | 1.37 | 0.02 | 1.76 | 1.412 |
| | | | | | | | 0.031 | | | | |

| Day 4 | | 8 | 9 | 10 | 11 | 12 | MEAN | Stdev | CV | % Bias | |
|---|---|---|---|---|---|---|---|---|---|---|---|
| 100 | 0 mg/mL | 1.362 | 1.375 | 1.364 | 1.386 | 0.041 | 1.32 | 0.03 | 2.03 | 2.0 | |
| ppm | 5 mg/mL | 1.43 | 1.424 | 1.452 | 1.382 | 0.042 | 1.36 | 0.04 | 3.21 | 1.5 | |
| MIT | 25 mg/mL | 1.412 | 1.423 | 1.39 | 1.398 | 0.041 | 1.36 | 0.02 | 1.48 | 1.0 | |
| | 50 mg/mL | 1.407 | 1.412 | 1.423 | 1.401 | 0.042 | 1.36 | 0.01 | 1.00 | 1.0 | |
| 50 | 0 mg/mL | 1.356 | 1.371 | 1.385 | 1.388 | 0.043 | 1.33 | 0.02 | 1.13 | 1.5 | |
| ppm | 5 mg/mL | 1.472 | 1.459 | 1.441 | 1.443 | 0.042 | 1.41 | 0.01 | 0.91 | 1.4 | |
| MIT | 25 mg/mL | 1.431 | 1.41 | 1.38 | 1.398 | 0.042 | 1.37 | 0.02 | 1.44 | 3.0 | |
| | 50 mg/mL | 1.555 | 1.531 | 1.48 | 1.6 | 0.042 | 1.47 | 0.07 | 4.91 | -7.2 | |
| | | | | | | 0.042 | | | | | |

| Day 14 | | 1 | 2 | 3 | 4 | 5 | 6 | MEAN | Stdev | CV | 7 |
|---|---|---|---|---|---|---|---|---|---|---|---|
| 100 | 0 mg/mL | 0.218 | 0.215 | 0.21 | 0.214 | 0.219 | 0.04 | 0.18 | 0.00 | 2.03 | 0.3 |
| ppm | 5 mg/mL | 1.479 | 1.506 | 1.389 | 1.39 | 1.577 | 0.04 | 1.43 | 0.08 | 5.62 | 1.447 |
| MIT | 25 mg/mL | 1.422 | 1.404 | 1.428 | 1.458 | 1.477 | 0.039 | 1.40 | 0.03 | 2.10 | 1.395 |
| | 50 mg/mL | 1.442 | 1.477 | 1.456 | 1.492 | 1.478 | 0.04 | 1.43 | 0.02 | 1.39 | 1.489 |
| 50 | 0 mg/mL | 0.272 | 0.267 | 0.265 | 0.283 | 0.286 | 0.039 | 0.24 | 0.01 | 4.02 | 0.287 |
| ppm | 5 mg/mL | 1.413 | 1.372 | 1.41 | 1.423 | 1.437 | 0.039 | 1.37 | 0.02 | 1.77 | 1.433 |
| MIT | 25 mg/mL | 1.413 | 1.41 | 1.413 | 1.422 | 1.427 | 0.035 | 1.38 | 0.01 | 0.52 | 1.428 |
| | 50 mg/mL | 1.434 | 1.444 | 1.427 | 1.431 | 1.432 | 0.04 | 1.39 | 0.01 | 0.46 | 1.413 |
| | | | | | | | 0.0395 | | | | |

| Day 14 | | 8 | 9 | 10 | 11 | 12 | MEAN | Stdev | CV | % Bias | |
|---|---|---|---|---|---|---|---|---|---|---|---|
| 100 | 0 mg/mL | 0.303 | 0.308 | 0.324 | 0.324 | 0.045 | 0.27 | 0.01 | 4.32 | -34.1 | |
| ppm | 5 mg/mL | 1.448 | 1.387 | 1.525 | 1.544 | 0.046 | 1.42 | 0.06 | 4.49 | 0.3 | |
| MIT | 25 mg/mL | 1.454 | 1.474 | 1.456 | 1.454 | 0.045 | 1.40 | 0.03 | 2.14 | -0.2 | |
| | 50 mg/mL | 1.51 | 1.464 | 1.486 | 1.48 | 0.045 | 1.44 | 0.02 | 1.15 | -0.8 | |
| 50 | 0 mg/mL | 0.292 | 0.306 | 0.317 | 0.314 | 0.045 | 0.26 | 0.01 | 6.14 | -8.8 | |
| ppm | 5 mg/mL | 1.422 | 1.429 | 1.438 | 1.435 | 0.046 | 1.39 | 0.01 | 0.45 | -1.0 | |
| MIT | 25 mg/mL | 1.435 | 1.431 | 1.407 | 1.426 | 0.046 | 1.38 | 0.01 | 0.78 | -0.2 | |
| | 50 mg/mL | 1.42 | 1.412 | 1.423 | 1.423 | 0.045 | 1.37 | 0.01 | 0.39 | 1.5 | |
| | | | | | | 0.045375 | | | | | |

As depicted below in Table 2, sarcosine oxidase (commercially offered for sale by Toyobo) enzyme activity is measured against various concentrations of MIT (biocide) and BSA (scavenger protein) over a period of 14 days (with absorbance measurements taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the MIT biocide. As can be clearly seen in Table 2, at days 4 and 14, the aqueous solutions (columns 1-5) comprising 5 mg/mL, 25 mg/mL, and 50 mg/mL concentrations of BSA show increased absorbance of the sarcosine oxidase enzyme (as compared to the samples containing 0 mg/mL of BSA). Such absorbance readings confirm the preservative effect of the BSA scavenger protein on the sarcosine oxidase enzyme activity in the presence of MIT biocide. In addition, solutions 7-11, which only contain BSA and no MIT biocide, also show increased (or at least maintained) sarcosine oxidase absorbance at days 4 and 14, which further illustrates BSA's preservative effect on sarcosine oxidase enzyme activity.

TABLE 2

Toyobo Sarcosine Oxidase Enzyme Absorbance with BSA and MIT

| Day 0 | BSA | 1 | 2 | 3 | 4 | 5 | 6 | MEAN | Stdev | CV | 7 |
|---|---|---|---|---|---|---|---|---|---|---|---|
| 100 | 0 mg/mL | 1.491 | 1.45 | 1.5 | 1.478 | 1.464 | 0.039 | 1.44 | 0.02 | 1.40 | 1.5 |
| ppm | 5 mg/mL | 1.437 | 1.434 | 1.433 | 1.43 | 1.438 | 0.04 | 1.39 | 0.00 | 0.23 | 1.436 |
| MIT | 25 mg/mL | 1.39 | 1.415 | 1.41 | 1.415 | 1.434 | 0.04 | 1.37 | 0.02 | 1.14 | 1.413 |
| | 50 mg/mL | 1.393 | 1.406 | 1.393 | 1.419 | 1.417 | 0.04 | 1.37 | 0.01 | 0.92 | 1.416 |
| 50 | 0 mg/mL | 1.463 | 1.462 | 1.447 | 1.446 | 1.462 | 0.04 | 1.42 | 0.01 | 0.61 | 1.439 |
| ppm | 5 mg/mL | 1.445 | 1.446 | 1.443 | 1.456 | 1.457 | 0.04 | 1.41 | 0.01 | 0.47 | 1.444 |
| MIT | 25 mg/mL | 1.432 | 1.423 | 1.425 | 1.431 | 1.427 | 0.04 | 1.39 | 0.00 | 0.28 | 1.448 |
| | 50 mg/mL | 1.439 | 1.435 | 1.441 | 1.396 | 1.415 | 0.04 | 1.39 | 0.02 | 1.39 | 1.387 |
| | | | | | | | 0.039875 | | | | |

TABLE 2-continued

Toyobo Sarcosine Oxidase Enzyme Absorbance with BSA and MIT

| Day 0 | | BSA | 8 | 9 | 10 | 11 | 12 | MEAN | Stdev | CV | % Bias |
|---|---|---|---|---|---|---|---|---|---|---|---|
| 100 ppm MIT | 0 mg/mL | | 1.471 | 1.424 | 1.412 | 1.426 | 0.047 | 1.40 | 0.04 | 2.67 | 2.6 |
| | 5 mg/mL | | 1.459 | 1.421 | 1.427 | 1.439 | 0.045 | 1.39 | 0.01 | 1.04 | 0.3 |
| | 25 mg/mL | | 1.447 | 1.422 | 1.418 | 1.443 | 0.046 | 1.38 | 0.02 | 1.11 | −0.7 |
| | 50 mg/mL | | 1.437 | 1.434 | 1.424 | 1.423 | 0.045 | 1.38 | 0.01 | 0.62 | −1.1 |
| 50 ppm MIT | 0 mg/mL | | 1.465 | 1.455 | 1.445 | 1.448 | 0.045 | 1.40 | 0.01 | 0.71 | 0.8 |
| | 5 mg/mL | | 1.45 | 1.459 | 1.485 | 1.463 | 0.046 | 1.41 | 0.02 | 1.11 | −0.3 |
| | 25 mg/mL | | 1.453 | 1.45 | 1.442 | 1.444 | 0.046 | 1.40 | 0.00 | 0.32 | −1.0 |
| | 50 mg/mL | | 1.402 | 1.388 | 1.408 | 1.406 | 0.047 | 1.35 | 0.01 | 0.74 | 2.4 |
| | | | | | | | 0.045875 | | | | |

| Day 4 | | | 1 | 2 | 3 | 4 | 5 | 6 | MEAN | Stdev | CV | 7 |
|---|---|---|---|---|---|---|---|---|---|---|---|---|
| 100 ppm MIT | 0 mg/mL | | 0.302 | 0.304 | 0.298 | 0.317 | 0.304 | 0.031 | 0.27 | 0.01 | 2.61 | 0.284 |
| | 5 mg/mL | | 0.952 | 0.938 | 0.967 | 0.949 | 0.972 | 0.03 | 0.92 | 0.01 | 1.50 | 0.933 |
| | 25 mg/mL | | 1.389 | 1.375 | 1.401 | 1.379 | 1.381 | 0.031 | 1.35 | 0.01 | 0.76 | 1.366 |
| | 50 mg/mL | | 1.412 | 1.401 | 1.39 | 1.416 | 1.405 | 0.032 | 1.37 | 0.01 | 0.74 | 1.384 |
| 50 ppm MIT | 0 mg/mL | | 0.277 | 0.275 | 0.272 | 0.283 | 0.282 | 0.032 | 0.25 | 0.00 | 1.89 | 0.27 |
| | 5 mg/mL | | 0.898 | 0.904 | 0.884 | 0.886 | 0.897 | 0.032 | 0.86 | 0.01 | 0.99 | 0.251 |
| | 25 mg/mL | | 1.409 | 1.394 | 1.393 | 1.392 | 1.395 | 0.032 | 1.37 | 0.01 | 0.51 | 1.388 |
| | 50 mg/mL | | 1.448 | 1.395 | 1.409 | 1.475 | 1.415 | 0.032 | 1.40 | 0.03 | 2.33 | 1.386 |
| | | | | | | | | 0.0315 | | | | |

| Day 4 | | | 8 | 9 | 10 | 11 | 12 | MEAN | Stdev | CV | % Bias |
|---|---|---|---|---|---|---|---|---|---|---|---|
| 100 ppm MIT | 0 mg/mL | | 0.277 | 0.291 | 0.282 | 0.288 | 0.041 | 0.13 | 0.01 | 4.27 | 115.9 |
| | 5 mg/mL | | 0.941 | 0.967 | n/a | 0.963 | 0.969 | 0.79 | 0.02 | 2.09 | 16.5 |
| | 25 mg/mL | | 1.381 | 1.402 | 1.382 | 1.388 | 0.041 | 1.23 | 0.01 | 1.06 | 10.4 |
| | 50 mg/mL | | 1.407 | 1.4 | 1.389 | 1.388 | 0.042 | 1.24 | 0.01 | 0.77 | 11.1 |
| 50 ppm MIT | 0 mg/mL | | 0.271 | 0.273 | 0.298 | 0.288 | 0.042 | 0.12 | 0.01 | 10.17 | 101.5 |
| | 5 mg/mL | | 0.247 | 0.255 | 0.261 | 0.267 | 0.043 | 0.10 | 0.01 | 8.08 | 775.9 |
| | 25 mg/mL | | 1.399 | 1.382 | 1.357 | 1.362 | 0.042 | 1.22 | 0.02 | 1.45 | 11.9 |
| | 50 mg/mL | | 1.428 | 1.403 | 1.415 | 1.372 | 0.042 | 1.24 | 0.02 | 1.80 | 12.4 |
| | | | | | | | 0.158 | | | | |

| Day 14 | | | 1 | 2 | 3 | 4 | 5 | 6 | MEAN | Stdev | CV | 7 |
|---|---|---|---|---|---|---|---|---|---|---|---|---|
| 100 ppm MIT | 0 mg/mL | | 0.163 | 0.176 | 0.168 | 0.172 | 0.176 | 0.049 | 0.13 | 0.01 | 4.29 | 0.158 |
| | 5 mg/mL | | 0.35 | 0.353 | 0.356 | 0.347 | 0.356 | 0.041 | 0.31 | 0.00 | 1.26 | 0.342 |
| | 25 mg/mL | | 1.468 | 1.449 | 1.465 | 1.427 | 1.445 | 0.04 | 1.41 | 0.02 | 1.18 | 1.443 |
| | 50 mg/mL | | 1.46 | 1.461 | 1.467 | 1.462 | 1.475 | 0.04 | 1.42 | 0.01 | 0.44 | 1.476 |
| 50 ppm MIT | 0 mg/mL | | 0.154 | 0.153 | 0.151 | 0.159 | 0.16 | 0.04 | 0.11 | 0.00 | 3.43 | 0.144 |
| | 5 mg/mL | | 0.324 | 0.328 | 0.323 | 0.332 | 0.343 | 0.04 | 0.29 | 0.01 | 2.80 | 0.329 |
| | 25 mg/mL | | 1.427 | 1.41 | 1.427 | 1.42 | 1.457 | 0.04 | 1.39 | 0.02 | 1.26 | 1.406 |
| | 50 mg/mL | | 1.474 | 1.448 | 1.445 | 1.478 | 1.48 | 0.04 | 1.42 | 0.02 | 1.20 | 1.436 |
| | | | | | | | | 0.04125 | | | | |

| Day 14 | | | 8 | 9 | 10 | 11 | 12 | MEAN | Stdev | CV | % Bias |
|---|---|---|---|---|---|---|---|---|---|---|---|
| 100 ppm MIT | 0 mg/mL | | 0.161 | 0.164 | 0.175 | 0.166 | 0.045 | 0.12 | 0.01 | 5.41 | 8.8 |
| | 5 mg/mL | | 0.353 | 0.351 | 0.382 | 0.368 | 0.046 | 0.31 | 0.02 | 5.04 | −0.8 |
| | 25 mg/mL | | 1.445 | 1.46 | 1.471 | 1.461 | 0.045 | 1.41 | 0.01 | 0.84 | −0.1 |
| | 50 mg/mL | | 1.446 | 1.464 | 1.474 | 1.469 | 0.046 | 1.42 | 0.01 | 0.85 | 0.2 |
| 50 ppm MIT | 0 mg/mL | | 0.154 | 0.152 | 0.154 | 0.155 | 0.045 | 0.11 | 0.00 | 4.23 | 7.4 |
| | 5 mg/mL | | 0.33 | 0.348 | 0.327 | 0.333 | 0.046 | 0.29 | 0.01 | 2.93 | 0.3 |
| | 25 mg/mL | | 1.41 | 1.429 | 1.404 | 1.403 | 0.046 | 1.36 | 0.01 | 0.79 | 1.6 |
| | 50 mg/mL | | 1.456 | 1.449 | 1.465 | 1.488 | 0.045 | 1.41 | 0.02 | 1.38 | 0.7 |
| | | | | | | | 0.0455 | | | | |

As depicted below in Table 3, sarcosine oxidase (commercially offered for sale by BBI Solutions) enzyme activity is measured against various concentrations of Proclin™ 300 (biocide) and BSA (scavenger protein) over a period of 14 days (with absorbance measurements taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the Proclin™ 300 biocide. While the level of preservation is not as pronounced as in Tables 1 and 2, at days 4 and 14, the aqueous solutions (columns 1-5) comprising 5 mg/mL, 25 mg/mL, and 50 mg/mL concentrations of BSA show increased absorbance of the sarcosine oxidase enzyme (as compared to the samples containing 0 mg/mL of BSA). Such absorbance readings confirm the preservative effect (albeit mild) of the BSA scavenger protein on the sarcosine oxidase enzyme activity in the presence of Proclin™ 300 biocide. In addition, solutions 7-11, which only contain BSA and no Proclin™ 300 biocide, also show increased (or at least maintained) sarcosine oxidase absorbance at days 4 and 14, which further illustrates BSA's preservative effect on sarcosine oxidase enzyme activity.

TABLE 3

BBI Solutions Sarcosine Oxidase Enzyme Absorbance with BSA and Proclin™ 300

| Day 0 | BSA | 1 | 2 | 3 | 4 | 5 | 6 | MEAN | Stdev | CV | 7 |
|---|---|---|---|---|---|---|---|---|---|---|---|
| 1.4% | 0 mg/mL | 1.289 | 1.285 | 1.329 | 1.331 | 1.287 | 0.04 | 1.26 | 0.02 | 1.89 | 1.419 |
| Proclin | 5 mg/mL | 1.424 | 1.416 | 1.408 | 1.411 | 1.416 | 0.04 | 1.38 | 0.01 | 0.44 | 1.444 |
| 300 | 25 mg/mL | 1.407 | 1.409 | 1.401 | 1.405 | 1.406 | 0.04 | 1.37 | 0.00 | 0.22 | 1.376 |
|  | 50 mg/mL | 1.389 | 1.413 | 1.373 | 1.381 | 1.382 | 0.04 | 1.35 | 0.02 | 1.13 | 1.396 |
| 0.7% | 0 mg/mL | 1.363 | 1.335 | 1.334 | 1.339 | 1.349 | 0.04 | 1.30 | 0.01 | 0.93 | 1.451 |
| Proclin | 5 mg/mL | 1.919 | 1.649 | 1.425 | 1.741 | 1.433 | 0.04 | 1.59 | 0.21 | 13.21 | 1.447 |
| 300 | 25 mg/mL | 1.335 | 1.377 | 1.382 | 1.385 | 1.407 | 0.04 | 1.34 | 0.03 | 1.96 | 1.429 |
|  | 50 mg/mL | 1.281 | 1.295 | 1.315 | 1.309 | 1.334 | 0.04 | 1.27 | 0.02 | 1.59 | 1.376 |
|  |  |  |  |  |  |  | 0.04 |  |  |  |  |

| Day 0 | BSA | 8 | 9 | 10 | 11 | 12 | MEAN | Stdev | CV | % Bias |
|---|---|---|---|---|---|---|---|---|---|---|
| 1.4% | 0 mg/mL | 1.411 | 1.399 | 1.43 | 1.42 | 0.047 | 1.37 | 0.01 | 0.84 | −7.7 |
| Proclin | 5 mg/mL | 1.464 | 1.437 | 1.453 | 1.458 | 0.046 | 1.40 | 0.01 | 0.77 | −2.1 |
| 300 | 25 mg/mL | 1.39 | 1.396 | 1.375 | 1.392 | 0.047 | 1.34 | 0.01 | 0.72 | 2.0 |
|  | 50 mg/mL | 1.402 | 1.394 | 1.401 | 1.397 | 0.047 | 1.35 | 0.00 | 0.26 | −0.3 |
| 0.7% | 0 mg/mL | 1.455 | 1.453 | 1.439 | 1.445 | 0.046 | 1.40 | 0.01 | 0.47 | −7.0 |
| Proclin | 5 mg/mL | 1.677 | 1.453 | 1.748 | 1.453 | 0.047 | 1.51 | 0.15 | 9.64 | 5.6 |
| 300 | 25 mg/mL | 1.441 | 1.415 | 1.398 | 1.406 | 0.046 | 1.37 | 0.02 | 1.26 | −2.5 |
|  | 50 mg/mL | 1.375 | 1.399 | 1.416 | 1.421 | 0.046 | 1.35 | 0.02 | 1.60 | −6.2 |
|  |  |  |  |  |  | 0.0465 |  |  |  |  |

| Day 4 |  | 1 | 2 | 3 | 4 | 5 | 6 | MEAN | Stdev | CV | 7 |
|---|---|---|---|---|---|---|---|---|---|---|---|
| 1.4% | 0 mg/mL | 0.04 | 0.037 | 0.031 | 0.034 | 0.035 | 0.03 | 0.00 | 0.00 | 70.40 | 1.382 |
| Proclin | 5 mg/mL | 0.052 | 0.049 | 0.043 | 0.046 | 0.047 | 0.03 | 0.02 | 0.00 | 20.04 | 1.446 |
| 300 | 25 mg/mL | 0.153 | 0.147 | 0.142 | 0.145 | 0.146 | 0.03 | 0.12 | 0.00 | 3.48 | 1.416 |
|  | 50 mg/mL | 0.288 | 0.287 | 0.278 | 0.291 | 0.289 | 0.031 | 0.26 | 0.01 | 1.97 | 1.38 |
| 0.7% | 0 mg/mL | 0.041 | 0.038 | 0.032 | 0.035 | 0.036 | 0.031 | 0.01 | 0.00 | 58.21 | 1.398 |
| Proclin | 5 mg/mL | 0.072 | 0.071 | 0.063 | 0.068 | 0.069 | 0.031 | 0.04 | 0.00 | 9.24 | 1.505 |
| 300 | 25 mg/mL | 0.27 | 0.266 | 0.268 | 0.273 | 0.274 | 0.031 | 0.24 | 0.00 | 1.40 | 1.45 |
|  | 50 mg/mL | 0.481 | 0.477 | 0.467 | 0.493 | 0.486 | 0.031 | 0.45 | 0.01 | 2.17 | 1.416 |
|  |  |  |  |  |  |  | 0.030625 |  |  |  |  |

| Day 4 |  | 8 | 9 | 10 | 11 | 12 | MEAN | Stdev | CV | % Bias |
|---|---|---|---|---|---|---|---|---|---|---|
| 1.4% | 0 mg/mL | 1.401 | 1.405 | 1.406 | 1.383 | 0.042 | 1.35 | 0.01 | 0.88 | −99.6 |
| Proclin | 5 mg/mL | 1.471 | 1.449 | 1.46 | 1.484 | 0.042 | 1.42 | 0.02 | 1.11 | −98.8 |
| 300 | 25 mg/mL | 1.421 | 1.436 | 1.431 | 1.426 | 0.041 | 1.38 | 0.01 | 0.57 | −91.6 |
|  | 50 mg/mL | 1.397 | 1.397 | 1.399 | 1.403 | 0.042 | 1.35 | 0.01 | 0.66 | −81.1 |
| 0.7% | 0 mg/mL | 1.397 | 1.398 | 1.424 | 1.435 | 0.042 | 1.37 | 0.02 | 1.31 | −99.6 |
| Proclin | 5 mg/mL | 1.507 | 1.518 | 1.472 | 1.484 | 0.05 | 1.45 | 0.02 | 1.29 | −97.4 |
| 300 | 25 mg/mL | 1.451 | 1.465 | 1.418 | 1.415 | 0.042 | 1.40 | 0.02 | 1.88 | −82.8 |
|  | 50 mg/mL | 1.425 | 1.435 | 1.402 | 1.421 | 0.042 | 1.38 | 0.01 | 0.88 | −67.3 |
|  |  |  |  |  |  | 0.043 |  |  |  |  |

| Day 14 |  | 1 | 2 | 3 | 4 | 5 | 6 | MEAN | Stdev | CV | 7 |
|---|---|---|---|---|---|---|---|---|---|---|---|
| 1.4% | 0 mg/mL | 0.039 | 0.038 | 0.034 | 0.04 | 0.041 | 0.044 | 0.00 | 0.00 | −128.66 | 0.272 |
| Proclin | 5 mg/mL | 0.04 | 0.039 | 0.034 | 0.037 | 0.041 | 0.041 | 0.00 | 0.00 | −120.66 | 1.527 |
| 300 | 25 mg/mL | 0.042 | 0.039 | 0.036 | 0.038 | 0.04 | 0.04 | 0.00 | 0.00 | −149.07 | 1.499 |
|  | 50 mg/mL | 0.047 | 0.04 | 0.042 | 0.043 | 0.046 | 0.04 | 0.00 | 0.00 | 53.17 | 1.467 |
| 0.7% | 0 mg/mL | 0.041 | 0.039 | 0.034 | 0.037 | 0.04 | 0.039 | −0.00 | 0.00 | −120.66 | 0.264 |
| Proclin | 5 mg/mL | 0.043 | 0.035 | 0.037 | 0.037 | 0.039 | 0.04 | 0.00 | 0.00 | −146.47 | 1.53 |
| 300 | 25 mg/mL | 0.047 | 0.044 | 0.041 | 0.043 | 0.046 | 0.04 | 0.00 | 0.00 | 64.53 | 1.498 |
|  | 50 mg/mL | 0.106 | 0.104 | 0.102 | 0.103 | 0.105 | 0.04 | 0.06 | 0.00 | 2.49 | 1.493 |
|  |  |  |  |  |  |  | 0.0405 |  |  |  |  |

| Day 14 |  | 8 | 9 | 10 | 11 | 12 | MEAN | Stdev | CV | % Bias |
|---|---|---|---|---|---|---|---|---|---|---|
| 1.4% | 0 mg/mL | 0.276 | 0.28 | 0.287 | 0.293 | 0.045 | 0.24 | 0.01 | 3.57 | −100.9 |
| Proclin | 5 mg/mL | 1.53 | 1.526 | 1.566 | 1.526 | 0.045 | 1.49 | 0.02 | 1.17 | −100.2 |
| 300 | 25 mg/mL | 1.497 | 1.533 | 1.539 | 1.525 | 0.045 | 1.47 | 0.02 | 1.32 | −100.1 |
|  | 50 mg/mL | 1.491 | 1.482 | 1.534 | 1.529 | 0.046 | 1.46 | 0.03 | 2.03 | −99.7 |
| 0.7% | 0 mg/mL | 0.275 | 0.274 | 0.284 | 0.282 | 0.045 | 0.23 | 0.01 | 3.42 | −101.0 |
| Proclin | 5 mg/mL | 1.542 | 1.526 | 1.538 | 1.535 | 0.046 | 1.49 | 0.01 | 0.43 | −100.1 |
| 300 | 25 mg/mL | 1.527 | 1.533 | 1.503 | 1.505 | 0.045 | 1.47 | 0.02 | 1.07 | −99.7 |
|  | 50 mg/mL | 1.499 | 1.505 | 1.513 | 1.541 | 0.046 | 1.46 | 0.02 | 1.28 | −95.7 |
|  |  |  |  |  |  | 0.045375 |  |  |  |  |

As depicted below in Table 4, sarcosine oxidase (commercially offered for sale by Toyobo) enzyme activity is measured against various concentrations of Proclin™ 300 (biocide) and BSA (scavenger protein) over a period of 14 days (with absorbance measurements taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the Proclin™ 300 biocide. At days 4 and 14, the aqueous solutions (columns 1-5) comprising 5 mg/mL, 25 mg/mL, and 50 mg/mL concentrations of BSA show increased absorbance of the sarcosine oxidase enzyme (as compared to the samples containing 0 mg/mL of BSA). Such absorbance readings confirm the preservative effect of the BSA scavenger protein on the sarcosine oxidase enzyme activity in the presence of Proclin™ 300 biocide. In addition, solutions 7-11, which only contain BSA and no Proclin™ 300 biocide, also show increased (or at least maintained) sarcosine oxidase absorbance at days 4 and 14, which further illustrates BSA's preservative effect on sarcosine oxidase enzyme activity.

TABLE 4

Toyobo Sarcosine Oxidase Enzyme Absorbance with BSA and Proclin ™ 300

| Day 0 | BSA | | 1 | 2 | 3 | 4 | 5 | 6 | MEAN | Stdev | CV | 7 |
|---|---|---|---|---|---|---|---|---|---|---|---|---|
| 1.4% | 0 | mg/mL | 1.333 | 1.33 | 1.365 | 1.34 | 1.361 | 0.041 | 1.30 | 0.02 | 1.24 | 1.406 |
| Proclin | 5 | mg/mL | 1.317 | 1.326 | 1.347 | 1.327 | 1.365 | 0.04 | 1.30 | 0.02 | 1.50 | 1.389 |
| 300 | 25 | mg/mL | 1.329 | 1.332 | 1.339 | 1.316 | 1.352 | 0.04 | 1.29 | 0.01 | 1.02 | 1.403 |
|  | 50 | mg/mL | 1.361 | 1.362 | 1.353 | 1.378 | 1.365 | 0.042 | 1.32 | 0.01 | 0.69 | 1.396 |
| 0.7% | 0 | mg/mL | 1.368 | 1.389 | 1.394 | 1.392 | 1.397 | 0.041 | 1.35 | 0.01 | 0.86 | 1.433 |
| Proclin | 5 | mg/mL | 1.472 | 1.394 | 1.377 | 1.387 | 1.405 | 0.041 | 1.37 | 0.04 | 2.76 | 1.419 |
| 300 | 25 | mg/mL | 1.41 | 1.427 | 1.4 | 1.413 | 1.413 | 0.041 | 1.37 | 0.01 | 0.70 | 1.443 |
|  | 50 | mg/mL | 1.422 | 1.41 | 1.391 | 1.422 | 1.409 | 0.042 | 1.37 | 0.01 | 0.93 | 1.418 |
|  |  |  |  |  |  |  |  | 0.041 |  |  |  |  |

| Day 0 | BSA | | 8 | 9 | 10 | 11 | 12 | MEAN | Stdev | CV | % Bias |
|---|---|---|---|---|---|---|---|---|---|---|---|
| 1.4% | 0 | mg/mL | 1.436 | 1.444 | 1.434 | 1.464 | 0.046 | 1.39 | 0.02 | 1.51 | −6.0 |
| Proclin | 5 | mg/mL | 1.397 | 1.397 | 1.427 | 1.404 | 0.047 | 1.35 | 0.01 | 1.07 | −4.4 |
| 300 | 25 | mg/mL | 1.403 | 1.426 | 1.429 | 1.44 | 0.048 | 1.37 | 0.02 | 1.21 | −5.8 |
|  | 50 | mg/mL | 1.409 | 1.41 | 1.444 | 1.448 | 0.047 | 1.37 | 0.02 | 1.69 | −3.7 |
| 0.7% | 0 | mg/mL | 1.45 | 1.438 | 1.446 | 1.462 | 0.046 | 1.40 | 0.01 | 0.80 | −3.6 |
| Proclin | 5 | mg/mL | 1.435 | 1.447 | 1.447 | 1.457 | 0.048 | 1.39 | 0.01 | 1.05 | −1.9 |
| 300 | 25 | mg/mL | 1.453 | 1.453 | 1.459 | 1.44 | 0.047 | 1.40 | 0.01 | 0.56 | −2.1 |
|  | 50 | mg/mL | 1.427 | 1.431 | 1.446 | 1.465 | 0.055 | 1.39 | 0.02 | 1.33 | −1.4 |
|  |  |  |  |  |  |  | 0.048 |  |  |  |  |

| Day 4 | | | 1 | 2 | 3 | 4 | 5 | 6 | MEAN | Stdev | CV | 7 |
|---|---|---|---|---|---|---|---|---|---|---|---|---|
| 1.4% | 0 | mg/mL | 0.143 | 0.138 | 0.132 | 0.141 | 0.138 | 0.032 | 0.11 | 0.00 | 3.94 | 0.279 |
| Proclin | 5 | mg/mL | 0.274 | 0.253 | 0.251 | 0.259 | 0.257 | 0.031 | 0.23 | 0.01 | 4.01 | 0.894 |
| 300 | 25 | mg/mL | 0.893 | 0.855 | 0.896 | 0.872 | 0.88 | 0.032 | 0.85 | 0.02 | 1.97 | 1.352 |
|  | 50 | mg/mL | 1.123 | 1.121 | 1.167 | 1.16 | 1.167 | 0.033 | 1.11 | 0.02 | 2.11 | 1.355 |
| 0.7% | 0 | mg/mL | 0.14 | 0.169 | 0.125 | 0.132 | 0.133 | 0.038 | 0.11 | 0.02 | 16.06 | 0.267 |
| Proclin | 5 | mg/mL | 0.23 | 0.231 | 0.222 | 0.239 | 0.252 | 0.032 | 0.20 | 0.01 | 5.62 | 0.829 |
| 300 | 25 | mg/mL | 0.826 | 0.819 | 0.822 | 0.829 | 0.844 | 0.032 | 0.80 | 0.01 | 1.22 | 1.337 |
|  | 50 | mg/mL | 1.124 | 1.098 | 1.113 | 1.116 | 1.136 | 0.033 | 1.08 | 0.01 | 1.29 | 1.354 |
|  |  |  |  |  |  |  |  | 0.032875 |  |  |  |  |

| Day 4 | | | 8 | 9 | 10 | 11 | 12 | MEAN | Stdev | CV | % Bias |
|---|---|---|---|---|---|---|---|---|---|---|---|
| 1.4% | 0 | mg/mL | 0.264 | 0.272 | 0.278 | 0.285 | 0.065 | 0.23 | 0.01 | 3.46 | −54.2 |
| Proclin | 5 | mg/mL | 0.884 | 0.896 | 0.908 | 0.935 | 0.042 | 0.86 | 0.02 | 2.29 | −73.7 |
| 300 | 25 | mg/mL | 1.372 | 1.385 | 1.362 | 1.354 | 0.042 | 1.32 | 0.01 | 1.04 | −35.9 |
|  | 50 | mg/mL | 1.369 | 1.383 | 1.36 | 1.362 | 0.041 | 1.32 | 0.01 | 0.82 | −15.6 |
| 0.7% | 0 | mg/mL | 0.265 | 0.27 | 0.287 | 0.277 | 0.046 | 0.23 | 0.01 | 3.93 | −53.1 |
| Proclin | 5 | mg/mL | 0.849 | 0.854 | 0.875 | 0.878 | 0.044 | 0.81 | 0.02 | 2.48 | −75.1 |
| 300 | 25 | mg/mL | 1.353 | 1.354 | 1.335 | 1.33 | 0.042 | 1.30 | 0.01 | 0.85 | −38.7 |
|  | 50 | mg/mL | 1.352 | 1.35 | 1.339 | 1.371 | 0.041 | 1.31 | 0.01 | 0.88 | −17.1 |
|  |  |  |  |  |  |  | 0.045 |  |  |  |  |

| Day 14 | | | 1 | 2 | 3 | 4 | 5 | 6 | MEAN | Stdev | CV | 7 |
|---|---|---|---|---|---|---|---|---|---|---|---|---|
| 1.4% | 0 | mg/mL | 0.052 | 0.051 | 0.049 | 0.049 | 0.053 | 0.046 | 0.00 | 0.00 | 38.26 | 0.143 |
| Proclin | 5 | mg/mL | 0.084 | 0.083 | 0.081 | 0.086 | 0.09 | 0.04 | 0.04 | 0.00 | 8.84 | 0.318 |
| 300 | 25 | mg/mL | 0.595 | 0.606 | 0.597 | 0.596 | 0.603 | 0.039 | 0.55 | 0.00 | 0.87 | 1.357 |
|  | 50 | mg/mL | 1.034 | 1.074 | 1.043 | 1.06 | 1.055 | 0.083 | 1.01 | 0.02 | 1.53 | 1.437 |
| 0.7% | 0 | mg/mL | 0.055 | 0.054 | 0.051 | 0.052 | 0.056 | 0.04 | 0.01 | 0.00 | 27.74 | 0.133 |
| Proclin | 5 | mg/mL | 0.077 | 0.077 | 0.073 | 0.078 | 0.079 | 0.041 | 0.03 | 0.00 | 7.43 | 0.288 |
| 300 | 25 | mg/mL | 0.53 | 0.523 | 0.523 | 0.544 | 0.535 | 0.04 | 0.48 | 0.01 | 1.83 | 1.371 |
|  | 50 | mg/mL | 0.948 | 0.957 | 0.954 | 0.943 | 0.947 | 0.04 | 0.90 | 0.01 | 0.62 | 1.445 |
|  |  |  |  |  |  |  |  | 0.046125 |  |  |  |  |

| Day 14 | | | 8 | 9 | 10 | 11 | 12 | MEAN | Stdev | CV | % Bias |
|---|---|---|---|---|---|---|---|---|---|---|---|
| 1.4% | 0 | mg/mL | 0.147 | 0.141 | 0.152 | 0.149 | 0.046 | 0.10 | 0.00 | 4.55 | −95.2 |
| Proclin | 5 | mg/mL | 0.317 | 0.316 | 0.331 | 0.403 | 0.047 | 0.29 | 0.04 | 12.96 | −86.6 |
| 300 | 25 | mg/mL | 1.368 | 1.435 | 1.372 | 1.399 | 0.051 | 1.34 | 0.03 | 2.34 | −58.6 |
|  | 50 | mg/mL | 1.432 | 1.429 | 1.445 | 1.436 | 0.046 | 1.39 | 0.01 | 0.44 | −27.4 |
| 0.7% | 0 | mg/mL | 0.138 | 0.141 | 0.145 | 0.145 | 0.059 | 0.09 | 0.01 | 5.53 | −91.9 |

TABLE 4-continued

Toyobo Sarcosine Oxidase Enzyme Absorbance with BSA and Proclin ™ 300

| Proclin 300 | 5 mg/mL | 0.295 | 0.302 | 0.314 | 0.303 | 0.046 | 0.25 | 0.01 | 3.86 | −87.8 |
|---|---|---|---|---|---|---|---|---|---|---|
| | 25 mg/mL | 1.421 | 1.363 | 1.372 | 1.401 | 0.047 | 1.34 | 0.02 | 1.83 | −63.7 |
| | 50 mg/mL | 1.544 | 1.434 | 1.475 | 1.436 | 0.046 | 1.42 | 0.05 | 3.26 | −36.3 |
| | | | | | | 0.0485 | | | | |

Table 5-8 depict aqueous solutions comprising varying concentrations of BSA (at concentrations of 0 mg/mL, 5 mg/mL, 25 mg/mL, and 50 mg/mL), varying concentrations of MIT (at concentrations of 50 parts per million and 100 parts per million) or Proclin™ 300 (at concentrations of 0.7% and 1.4%) biocide over a particular time period (measurements were taken at days 0, 4, and 14 after exposure of the enzyme(s) to the particular aqueous solutions) and the associated enzyme absorbance measurements for creatininase (commercially offered for sale by BBI Solutions and Toyobo). Absorbance measurements of the creatininase enzyme(s) were taken via spectrophotometer for each aqueous solution (represented as columns 1-5 in Tables 5-8—column 6 is a blank), the absorbance being directly proportional to the enzyme activity being measured-which for Tables 5-8 is creatininase enzyme activity. Accordingly, the higher the absorbance measurement, the higher the enzyme activity of creatininase. Columns 7-11 represent five replicate readings in which the solution only contains BSA (i.e., there is no biocide(s) present in the solution). In addition, the mean values, standard deviations, and coefficients of variation are all presented for the enzyme activity/absorbance of each aqueous solution. All measurements were taken at 37° C.

As depicted in Table 5, creatininase (commercially offered for sale by BBI Solutions) enzyme activity is measured against various concentrations of MIT (biocide) and BSA (scavenger protein) over a period of 14 days (with absorbance measurement taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the MIT biocide. As can be clearly seen in Table 5, at days 4 and 14, the aqueous solutions (columns 1-5) comprising 5 mg/mL, 25 mg/mL, and 50 mg/mL concentrations of BSA show increased absorbance of the creatininase enzyme (as compared to samples containing 0 mg/mL of BSA). The creatininase absorbance measurement is highest at BSA concentrations of 5 mg/mL, but all concentrations show increased (even if mild) absorbance measurements. Such absorbance readings confirm that preservative effect of the BSA scavenger protein on the creatininase enzyme activity in the presence of the MIT biocide. In addition, solutions 7-11, which only contain BSA and no MIT biocide, also show increased (or at least maintained) creatininase absorbance at days 4 and 14 (with the highest absorbance being measured at BSA concentrations of 5 mg/mL), which further illustrate BSA's preservative effect on creatininase enzyme activity.

TABLE 5

BBI Solutions Creatininase Enzyme Absorbance with BSA and MIT

| Day 0 | BSA | 1 | 2 | 3 | 4 | 5 | 6 | MEAN | Stdev | CV | 7 |
|---|---|---|---|---|---|---|---|---|---|---|---|
| 100 ppm MIT | 0 mg/mL | 0.765 | 0.721 | 0.731 | 0.712 | 0.723 | 0.215 | 0.53 | 0.02 | 3.88 | 0.755 |
| | 5 mg/mL | 0.839 | 0.784 | 0.778 | 0.782 | 0.797 | 0.204 | 0.59 | 0.03 | 4.22 | 0.773 |
| | 25 mg/mL | 0.785 | 0.72 | 0.705 | 0.727 | 0.751 | 0.205 | 0.54 | 0.03 | 5.84 | 0.705 |
| | 50 mg/mL | 0.749 | 0.669 | 0.673 | 0.678 | 0.704 | 0.196 | 0.49 | 0.03 | 6.77 | 0.686 |
| 50 ppm MIT | 0 mg/mL | 0.663 | 0.662 | 0.668 | 0.62 | 0.649 | 0.189 | 0.45 | 0.02 | 4.31 | 0.642 |
| | 5 mg/mL | 0.774 | 0.737 | 0.726 | 0.733 | 0.74 | 0.2 | 0.54 | 0.02 | 3.45 | 0.717 |
| | 25 mg/mL | 0.751 | 0.713 | 0.818 | 0.713 | 0.733 | 0.199 | 0.54 | 0.04 | 7.99 | 0.736 |
| | 50 mg/mL | 0.773 | 0.779 | 0.748 | 0.755 | 0.766 | 0.207 | 0.56 | 0.01 | 2.26 | 0.759 |
| | | | | | | | 0.202 | | | | |

| Day 0 | BSA | 8 | 9 | 10 | 11 | 12 | MEAN | Stdev | CV | % Bias |
|---|---|---|---|---|---|---|---|---|---|---|
| 100 ppm MIT | 0 mg/mL | 0.703 | 0.759 | 0.74 | 0.729 | 0.223 | 0.53 | 0.02 | 4.30 | 0.7 |
| | 5 mg/mL | 0.767 | 0.759 | 0.781 | 0.761 | 0.214 | 0.56 | 0.01 | 1.62 | 6.8 |
| | 25 mg/mL | 0.688 | 0.694 | 0.72 | 0.733 | 0.208 | 0.50 | 0.02 | 3.74 | 8.0 |
| | 50 mg/mL | 0.661 | 0.68 | 0.708 | 0.702 | 0.207 | 0.48 | 0.02 | 3.92 | 3.7 |
| 50 ppm MIT | 0 mg/mL | 0.63 | 0.658 | 0.664 | 0.63 | 0.202 | 0.43 | 0.02 | 3.63 | 4.1 |
| | 5 mg/mL | 0.707 | 0.707 | 0.75 | 0.728 | 0.208 | 0.51 | 0.02 | 3.53 | 6.0 |
| | 25 mg/mL | 0.712 | 0.709 | 0.752 | 0.746 | 0.211 | 0.52 | 0.02 | 3.78 | 4.8 |
| | 50 mg/mL | 0.723 | 0.742 | 0.773 | 0.777 | 0.224 | 0.54 | 0.02 | 4.14 | 3.6 |
| | | | | | | 0.212 | | | | |

| Day 4 | | 1 | 2 | 3 | 4 | 5 | 6 | MEAN | Stdev | CV | 7 |
|---|---|---|---|---|---|---|---|---|---|---|---|
| 100 ppm MIT | 0 mg/mL | 0.616 | 0.604 | 0.597 | 0.597 | 0.523 | 0.224 | 0.38 | 0.04 | 9.76 | 0.615 |
| | 5 mg/mL | 0.919 | 0.895 | 0.917 | 0.914 | 0.954 | 0.207 | 0.71 | 0.02 | 3.01 | 0.927 |
| | 25 mg/mL | 0.815 | 0.793 | 0.796 | 0.803 | 0.82 | 0.203 | 0.60 | 0.01 | 1.98 | 0.793 |
| | 50 mg/mL | 0.709 | 0.7 | 0.675 | 0.691 | 0.702 | 0.206 | 0.49 | 0.01 | 2.70 | 0.647 |
| 50 ppm MIT | 0 mg/mL | 0.654 | 0.633 | 0.52 | 0.638 | 0.638 | 0.205 | 0.41 | 0.05 | 13.43 | 0.654 |
| | 5 mg/mL | 0.972 | 0.953 | 0.913 | 0.948 | 0.937 | 0.21 | 0.73 | 0.02 | 2.96 | 0.95 |
| | 25 mg/mL | 0.806 | 0.821 | 0.806 | 0.821 | 0.855 | 0.208 | 0.61 | 0.02 | 3.27 | 0.821 |
| | 50 mg/mL | 0.659 | 0.673 | 0.665 | 0.672 | 0.658 | 0.219 | 0.46 | 0.01 | 1.54 | 0.621 |

TABLE 5-continued

BBI Solutions Creatininase Enzyme Absorbance with BSA and MIT 0.210

| Day 4 | | | 8 | 9 | 10 | 11 | 12 | MEAN | Stdev | CV | % Bias |
|---|---|---|---|---|---|---|---|---|---|---|---|
| 100 | 0 | mg/mL | 0.56 | 0.599 | 0.625 | 0.604 | 0.226 | 0.39 | 0.02 | 6.43 | −2.3 |
| ppm | 5 | mg/mL | 0.89 | 0.906 | 0.925 | 0.892 | 0.212 | 0.69 | 0.02 | 2.53 | 2.3 |
| MIT | 25 | mg/mL | 0.779 | 0.783 | 0.8 | 0.814 | 0.206 | 0.58 | 0.01 | 2.41 | 2.7 |
| | 50 | mg/mL | 0.629 | 0.631 | 0.657 | 0.637 | 0.208 | 0.43 | 0.01 | 2.75 | 14.0 |
| 50 | 0 | mg/mL | 0.598 | 0.632 | 0.598 | 0.558 | 0.214 | 0.39 | 0.04 | 9.33 | 3.3 |
| ppm | 5 | mg/mL | 0.906 | 0.917 | 0.926 | 0.911 | 0.211 | 0.71 | 0.02 | 2.45 | 3.8 |
| MIT | 25 | mg/mL | 0.794 | 0.77 | 0.821 | 0.793 | 0.217 | 0.59 | 0.02 | 3.69 | 4.5 |
| | 50 | mg/mL | 0.592 | 0.597 | 0.625 | 0.622 | 0.222 | 0.40 | 0.02 | 3.93 | 14.7 |
| | | | | | | | 0.215 | | | | |

| Day 14 | | | 1 | 2 | 3 | 4 | 5 | 6 | MEAN | Stdev | CV | 7 |
|---|---|---|---|---|---|---|---|---|---|---|---|---|
| 100 | 0 | mg/mL | 0.755 | 0.699 | 0.714 | 0.707 | 0.716 | 0.282 | 0.45 | 0.02 | 4.81 | 0.714 |
| ppm | 5 | mg/mL | 1.099 | 1.043 | 1.031 | 1.064 | 1.075 | 0.265 | 0.79 | 0.03 | 3.37 | 1.061 |
| MIT | 25 | mg/mL | 0.917 | 0.892 | 0.889 | 0.911 | 0.917 | 0.261 | 0.64 | 0.01 | 2.15 | 0.91 |
| | 50 | mg/mL | 0.755 | 0.744 | 0.718 | 0.744 | 0.755 | 0.261 | 0.47 | 0.02 | 3.19 | 0.74 |
| 50 | 0 | mg/mL | 0.732 | 0.689 | 0.701 | 0.686 | 0.725 | 0.26 | 0.44 | 0.02 | 4.78 | 0.742 |
| ppm | 5 | mg/mL | 1.1 | 1.067 | 1.062 | 1.08 | 1.103 | 0.272 | 0.81 | 0.02 | 2.29 | 1.062 |
| MIT | 25 | mg/mL | 0.946 | 0.906 | 0.898 | 0.922 | 0.928 | 0.27 | 0.65 | 0.02 | 2.90 | 0.931 |
| | 50 | mg/mL | 0.739 | 0.723 | 0.714 | 0.722 | 0.751 | 0.279 | 0.46 | 0.01 | 3.24 | 0.745 |
| | | | | | | | | 0.269 | | | | |

| Day 14 | | | 8 | 9 | 10 | 11 | 12 | MEAN | Stdev | CV | % Bias |
|---|---|---|---|---|---|---|---|---|---|---|---|
| 100 | 0 | mg/mL | 0.589 | 0.696 | 0.678 | 0.707 | 0.276 | 0.42 | 0.05 | 12.12 | 7.0 |
| ppm | 5 | mg/mL | 1.054 | 1.018 | 1.054 | 1.051 | 0.254 | 0.79 | 0.02 | 2.14 | 0.3 |
| MIT | 25 | mg/mL | 0.907 | 0.879 | 0.898 | 0.905 | 0.249 | 0.64 | 0.01 | 1.93 | −1.0 |
| | 50 | mg/mL | 0.737 | 0.713 | 0.724 | 0.724 | 0.246 | 0.47 | 0.01 | 2.33 | 0.7 |
| 50 | 0 | mg/mL | 0.722 | 0.709 | 0.72 | 0.732 | 0.249 | 0.47 | 0.01 | 2.68 | −6.5 |
| ppm | 5 | mg/mL | 1.055 | 1.027 | 1.067 | 1.069 | 0.254 | 0.80 | 0.02 | 2.14 | 1.8 |
| MIT | 25 | mg/mL | 0.918 | 0.882 | 0.905 | 0.92 | 0.258 | 0.65 | 0.02 | 2.87 | −0.5 |
| | 50 | mg/mL | 0.73 | 0.711 | 0.727 | 0.732 | 0.267 | 0.47 | 0.01 | 2.58 | −2.4 |
| | | | | | | | 0.257 | | | | |

As depicted in Table 6, creatininase (commercially offered for sale by Toyobo) enzyme activity is measured against various concentrations of MIT (biocide) and BSA (scavenger protein) over a period of 14 days (with absorbance measurement taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the MIT biocide. As can be clearly seen in Table 6, at days 4 and 14, the aqueous solutions (columns 1-5) comprising 5 mg/mL, 25 mg/mL, and 50 mg/mL concentrations of BSA show increased absorbance of the creatininase enzyme (as compared to samples containing 0 mg/mL of BSA). The creatininase absorbance measurement is highest at BSA concentrations of 5 mg/mL, but all concentrations show increased (even if mild) absorbance measurements. Such absorbance readings confirm that preservative effect of the BSA scavenger protein on the creatininase enzyme activity in the presence of the MIT biocide. In addition, solutions 7-11, which only contain BSA and no MIT biocide, also show increased (or at least maintained) creatininase absorbance at days 4 and 14 (with the highest absorbance being measured at BSA concentrations of 5 mg/mL), which further illustrate BSA's preservative effect on creatininase enzyme activity.

TABLE 6

Toyobo Creatininase Enzyme Absorbance with BSA and MIT

| Day 0 | BSA | | 1 | 2 | 3 | 4 | 5 | 6 | MEAN | Stdev | CV | 7 |
|---|---|---|---|---|---|---|---|---|---|---|---|---|
| 100 | 0 | mg/mL | 0.937 | 0.871 | 0.866 | 0.827 | 0.836 | 0.217 | 0.67 | 0.04 | 6.50 | 0.842 |
| ppm | 5 | mg/mL | 0.922 | 0.849 | 0.843 | 0.844 | 0.859 | 0.197 | 0.66 | 0.03 | 5.04 | 0.826 |
| MIT | 25 | mg/mL | 0.905 | 0.838 | 0.807 | 0.795 | 0.811 | 0.196 | 0.63 | 0.04 | 7.02 | 0.775 |
| | 50 | mg/mL | 0.867 | 0.794 | 0.799 | 0.792 | 0.771 | 0.195 | 0.60 | 0.04 | 6.05 | 0.757 |
| 50 | 0 | mg/mL | 0.846 | 0.775 | 0.735 | 0.721 | 0.713 | 0.189 | 0.56 | 0.05 | 9.83 | 0.736 |
| ppm | 5 | mg/mL | 0.893 | 0.808 | 0.806 | 0.812 | 0.843 | 0.199 | 0.63 | 0.04 | 5.88 | 0.791 |
| MIT | 25 | mg/mL | 0.895 | 0.829 | 0.788 | 0.82 | 0.831 | 0.203 | 0.63 | 0.04 | 6.17 | 0.767 |
| | 50 | mg/mL | 0.905 | 0.862 | 0.847 | 0.863 | 0.895 | 0.22 | 0.67 | 0.02 | 3.64 | 0.845 |
| | | | | | | | | 0.202 | | | | |

| Day 0 | BSA | | 8 | 9 | 10 | 11 | 12 | MEAN | Stdev | CV | % Bias |
|---|---|---|---|---|---|---|---|---|---|---|---|
| 100 | 0 | mg/mL | 0.836 | 0.841 | 0.851 | 0.884 | 0.229 | 0.64 | 0.02 | 3.02 | 3.8 |
| ppm | 5 | mg/mL | 0.806 | 0.802 | 0.845 | 0.845 | 0.204 | 0.61 | 0.02 | 3.34 | 7.6 |
| MIT | 25 | mg/mL | 0.751 | 0.768 | 0.799 | 0.806 | 0.203 | 0.57 | 0.02 | 3.97 | 10.4 |

TABLE 6-continued

Toyobo Creatininase Enzyme Absorbance with BSA and MIT

|  |  | 1 | 2 | 3 | 4 | 5 | 6 | MEAN | Stdev | CV | 7 |
|---|---|---|---|---|---|---|---|---|---|---|---|
|  | 50 mg/mL | 0.735 | 0.735 | 0.782 | 0.778 | 0.203 |  | 0.55 | 0.02 | 4.12 | 10.1 |
| 50 | 0 mg/mL | 0.684 | 0.711 | 0.731 | 0.707 | 0.201 |  | 0.50 | 0.02 | 4.13 | 10.4 |
| ppm | 5 mg/mL | 0.78 | 0.787 | 0.823 | 0.825 | 0.209 |  | 0.59 | 0.02 | 3.58 | 6.6 |
| MIT | 25 mg/mL | 0.776 | 0.77 | 0.817 | 0.824 | 0.209 |  | 0.58 | 0.03 | 4.72 | 8.6 |
|  | 50 mg/mL | 0.823 | 0.839 | 0.878 | 0.87 | 0.222 |  | 0.64 | 0.02 | 3.54 | 4.9 |
|  |  |  |  |  |  | 0.210 |  |  |  |  |  |

| Day 4 |  | 1 | 2 | 3 | 4 | 5 | 6 | MEAN | Stdev | CV | 7 |
|---|---|---|---|---|---|---|---|---|---|---|---|
| 100 | 0 mg/mL | 0.745 | 0.768 | 0.763 | 0.748 | 0.792 | 0.235 | 0.55 | 0.02 | 3.42 | 0.767 |
| ppm | 5 mg/mL | 0.998 | 0.974 | 1.006 | 1.008 | 1.031 | 0.205 | 0.79 | 0.02 | 2.59 | 0.996 |
| MIT | 25 mg/mL | 0.871 | 0.863 | 0.869 | 0.86 | 0.866 | 0.202 | 0.65 | 0.00 | 0.68 | 0.837 |
|  | 50 mg/mL | 0.773 | 0.775 | 0.754 | 0.734 | 0.742 | 0.203 | 0.54 | 0.02 | 3.36 | 0.729 |
| 50 | 0 mg/mL | 0.777 | 0.754 | 0.767 | 0.743 | 0.77 | 0.201 | 0.55 | 0.01 | 2.47 | 0.77 |
| ppm | 5 mg/mL | 1.031 | 0.998 | 1.012 | 1.044 | 1.01 | 0.212 | 0.81 | 0.02 | 2.27 | 1.028 |
| MIT | 25 mg/mL | 0.867 | 0.847 | 0.853 | 0.878 | 0.873 | 0.209 | 0.65 | 0.01 | 2.02 | 0.872 |
|  | 50 mg/mL | 0.737 | 0.728 | 0.749 | 0.75 | 0.765 | 0.233 | 0.53 | 0.01 | 2.64 | 0.729 |
|  |  |  |  |  |  |  | 0.213 |  |  |  |  |

| Day 4 |  | 8 | 9 | 10 | 11 | 12 | MEAN | Stdev | CV | % Bias |
|---|---|---|---|---|---|---|---|---|---|---|
| 100 | 0 mg/mL | 0.72 | 0.586 | 0.737 | 0.775 | 0.229 | 0.50 | 0.08 | 15.27 | 9.8 |
| ppm | 5 mg/mL | 0.965 | 0.967 | 1.015 | 1.005 | 0.215 | 0.77 | 0.02 | 2.92 | 2.2 |
| MIT | 25 mg/mL | 0.819 | 0.821 | 0.853 | 0.842 | 0.208 | 0.62 | 0.01 | 2.32 | 5.6 |
|  | 50 mg/mL | 0.711 | 0.714 | 0.742 | 0.72 | 0.21 | 0.51 | 0.01 | 2.47 | 7.0 |
| 50 | 0 mg/mL | 0.708 | 0.613 | 0.744 | 0.693 | 0.208 | 0.49 | 0.06 | 12.23 | 12.2 |
| ppm | 5 mg/mL | 1.018 | 1.013 | 1.041 | 1.02 | 0.213 | 0.81 | 0.01 | 1.35 | -0.2 |
| MIT | 25 mg/mL | 0.851 | 0.852 | 0.866 | 0.845 | 0.215 | 0.64 | 0.01 | 1.76 | 1.5 |
|  | 50 mg/mL | 0.721 | 0.727 | 0.759 | 0.76 | 0.227 | 0.52 | 0.02 | 3.58 | 1.9 |
|  |  |  |  |  |  | 0.216 |  |  |  |  |

| Day 14 |  | 1 | 2 | 3 | 4 | 5 | 6 | MEAN | Stdev | CV | 7 |
|---|---|---|---|---|---|---|---|---|---|---|---|
| 100 | 0 mg/mL | 0.794 | 0.774 | 0.784 | 0.73 | 0.78 | 0.242 | 0.54 | 0.02 | 4.56 | 0.77 |
| ppm | 5 mg/mL | 1.155 | 1.123 | 1.105 | 1.133 | 1.156 | 0.227 | 0.91 | 0.02 | 2.40 | 1.089 |
| MIT | 25 mg/mL | 0.997 | 0.966 | 0.95 | 0.992 | 0.976 | 0.223 | 0.75 | 0.02 | 2.57 | 0.961 |
|  | 50 mg/mL | 0.854 | 0.822 | 0.792 | 0.828 | 0.832 | 0.223 | 0.60 | 0.02 | 3.74 | 0.8 |
| 50 | 0 mg/mL | 0.828 | 0.801 | 0.702 | 0.794 | 0.79 | 0.22 | 0.55 | 0.05 | 8.60 | 0.754 |
| ppm | 5 mg/mL | 1.13 | 1.104 | 1.098 | 1.12 | 1.117 | 0.229 | 0.88 | 0.01 | 1.45 | 1.098 |
| MIT | 25 mg/mL | 1.021 | 0.986 | 0.982 | 1.025 | 0.996 | 0.232 | 0.77 | 0.02 | 2.57 | 0.926 |
|  | 50 mg/mL | 0.814 | 0.793 | 0.789 | 0.796 | 0.804 | 0.237 | 0.57 | 0.01 | 1.74 | 0.769 |
|  |  |  |  |  |  |  | 0.229 |  |  |  |  |

| Day 14 |  | 8 | 9 | 10 | 11 | 12 | MEAN | Stdev | CV | % Bias |
|---|---|---|---|---|---|---|---|---|---|---|
| 100 | 0 mg/mL | 0.727 | 0.732 | 0.721 | 0.72 | 0.23 | 0.52 | 0.02 | 4.00 | 5.1 |
| ppm | 5 mg/mL | 1.089 | 1.072 | 1.098 | 1.083 | 0.212 | 0.87 | 0.01 | 1.10 | 4.1 |
| MIT | 25 mg/mL | 0.95 | 0.904 | 0.939 | 0.946 | 0.21 | 0.72 | 0.02 | 2.99 | 3.3 |
|  | 50 mg/mL | 0.789 | 0.756 | 0.778 | 0.774 | 0.209 | 0.56 | 0.02 | 2.94 | 6.0 |
| 50 | 0 mg/mL | 0.708 | 0.727 | 0.719 | 0.71 | 0.21 | 0.51 | 0.02 | 3.67 | 9.3 |
| ppm | 5 mg/mL | 1.137 | 1.087 | 1.119 | 1.145 | 0.213 | 0.90 | 0.02 | 2.75 | -1.7 |
| MIT | 25 mg/mL | 0.932 | 0.887 | 0.923 | 0.916 | 0.219 | 0.70 | 0.02 | 2.52 | 10.4 |
|  | 50 mg/mL | 0.778 | 0.743 | 0.773 | 0.764 | 0.232 | 0.55 | 0.01 | 2.47 | 3.9 |
|  |  |  |  |  |  | 0.217 |  |  |  |  |

As depicted in Table 7, creatininase (commercially offered for sale by BBI Solutions) enzyme activity is measured against various concentrations of Proclin™ 300 (biocide) and BSA (scavenger protein) over a period of 14 days (with absorbance measurement taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the Proclin™ 300 biocide. As can be seen in Table 7, at day 4 and at Proclin™ 300 biocide concentrations of 0.7%, the aqueous solutions (columns 1-5) comprising 5 mg/mL, 25 mg/mL, and 50 mg/mL concentrations of BSA show a mild increase in the absorbance of the creatininase enzyme (as compared to samples containing 0 mg/mL of BSA). At day 14, the creatininase enzyme activity remains unaffected by the presence of BSA in the preservation fluids. However, solutions 7-11, which only contain BSA and no Proclin™ 300 biocide, show increased (or at least maintained) creatininase absorbance at days 4 and 14 (with the highest absorbance being measured at BSA concentrations of 5 mg/mL), which illustrates BSA's preservative effect on creatininase enzyme activity.

TABLE 7

BBI Solutions Creatininase Enzyme Absorbance with BSA and Proclin ™ 300

| Day 0 | BSA | 1 | 2 | 3 | 4 | 5 | 6 | MEAN | Stdev | CV | 7 |
|---|---|---|---|---|---|---|---|---|---|---|---|

TABLE 7-continued

BBI Solutions Creatininase Enzyme Absorbance with BSA and Proclin™ 300

| | BSA | 1 | 2 | 3 | 4 | 5 | 6 | MEAN | Stdev | CV | 7 |
|---|---|---|---|---|---|---|---|---|---|---|---|
| 1.4% Proclin 300 | 0 mg/mL | 0.766 | 0.695 | 0.726 | 0.658 | 0.712 | 0.218 | 0.51 | 0.04 | 7.86 | 0.702 |
| | 5 mg/mL | 0.711 | 0.664 | 0.645 | 0.651 | 0.647 | 0.198 | 0.46 | 0.03 | 6.01 | 0.652 |
| | 25 mg/mL | 0.667 | 0.613 | 0.6 | 0.607 | 0.61 | 0.193 | 0.41 | 0.03 | 6.54 | 0.627 |
| | 50 mg/mL | 0.647 | 0.598 | 0.583 | 0.592 | 0.607 | 0.199 | 0.40 | 0.02 | 6.22 | 0.606 |
| 0.7% Proclin 300 | 0 mg/mL | 0.64 | 0.6 | 0.6 | 0.585 | 0.623 | 0.197 | 0.40 | 0.02 | 5.39 | 0.602 |
| | 5 mg/mL | 0.718 | 0.669 | 0.658 | 0.668 | 0.685 | 0.209 | 0.47 | 0.02 | 4.97 | 0.658 |
| | 25 mg/mL | 0.733 | 0.656 | 0.643 | 0.652 | 0.667 | 0.206 | 0.46 | 0.04 | 7.78 | 0.669 |
| | 50 mg/mL | 0.716 | 0.679 | 0.697 | 0.713 | 0.706 | 0.226 | 0.50 | 0.01 | 3.00 | 0.682 |
| | | | | | | | 0.206 | | | | |

| Day 0 | BSA | 8 | 9 | 10 | 11 | 12 | MEAN | Stdev | CV | % Bias |
|---|---|---|---|---|---|---|---|---|---|---|
| 1.4% Proclin 300 | 0 mg/mL | 0.682 | 0.685 | 0.67 | 0.698 | 0.223 | 0.47 | 0.01 | 2.73 | 7.2 |
| | 5 mg/mL | 0.65 | 0.644 | 0.679 | 0.656 | 0.211 | 0.44 | 0.01 | 3.05 | 3.9 |
| | 25 mg/mL | 0.613 | 0.607 | 0.624 | 0.644 | 0.207 | 0.41 | 0.01 | 3.50 | 1.5 |
| | 50 mg/mL | 0.593 | 0.598 | 0.617 | 0.624 | 0.212 | 0.39 | 0.01 | 3.29 | 1.9 |
| 0.7% Proclin 300 | 0 mg/mL | 0.573 | 0.604 | 0.598 | 0.584 | 0.209 | 0.38 | 0.01 | 3.52 | 7.2 |
| | 5 mg/mL | 0.656 | 0.654 | 0.693 | 0.67 | 0.212 | 0.45 | 0.02 | 3.60 | 5.1 |
| | 25 mg/mL | 0.654 | 0.645 | 0.676 | 0.685 | 0.219 | 0.45 | 0.02 | 3.53 | 3.1 |
| | 50 mg/mL | 0.675 | 0.682 | 0.716 | 0.716 | 0.231 | 0.48 | 0.02 | 4.20 | 3.7 |
| | | | | | | 0.216 | | | | |

| Day 4 | | 1 | 2 | 3 | 4 | 5 | 6 | MEAN | Stdev | CV | 7 |
|---|---|---|---|---|---|---|---|---|---|---|---|
| 1.4% Proclin 300 | 0 mg/mL | 0.282 | 0.276 | 0.273 | 0.272 | 0.275 | 0.228 | 0.06 | 0.00 | 6.54 | 0.594 |
| | 5 mg/mL | 0.256 | 0.246 | 0.248 | 0.245 | 0.25 | 0.211 | 0.03 | 0.00 | 13.11 | 0.863 |
| | 25 mg/mL | 0.24 | 0.228 | 0.227 | 0.22 | 0.226 | 0.208 | 0.01 | 0.01 | 58.59 | 0.757 |
| | 50 mg/mL | 0.239 | 0.225 | 0.219 | 0.22 | 0.221 | 0.211 | 0.01 | 0.01 | 91.25 | 0.671 |
| 0.7% Proclin 300 | 0 mg/mL | 0.28 | 0.267 | 0.229 | 0.26 | 0.268 | 0.21 | 0.05 | 0.02 | 42.56 | 0.619 |
| | 5 mg/mL | 0.303 | 0.296 | 0.301 | 0.3 | 0.314 | 0.217 | 0.09 | 0.01 | 7.77 | 0.886 |
| | 25 mg/mL | 0.296 | 0.288 | 0.281 | 0.284 | 0.288 | 0.216 | 0.07 | 0.01 | 7.87 | 0.783 |
| | 50 mg/mL | 0.308 | 0.292 | 0.29 | 0.296 | 0.299 | 0.225 | 0.08 | 0.01 | 8.70 | 0.671 |
| | | | | | | | 0.216 | | | | |

| Day 4 | | 8 | 9 | 10 | 11 | 12 | MEAN | Stdev | CV | % Bias |
|---|---|---|---|---|---|---|---|---|---|---|
| 1.4% Proclin 300 | 0 mg/mL | 0.576 | 0.601 | 0.592 | 0.571 | 0.225 | 0.36 | 0.01 | 3.49 | −83.6 |
| | 5 mg/mL | 0.829 | 0.895 | 0.929 | 0.882 | 0.223 | 0.65 | 0.04 | 5.59 | −94.9 |
| | 25 mg/mL | 0.715 | 0.735 | 0.756 | 0.767 | 0.221 | 0.52 | 0.02 | 3.98 | −97.6 |
| | 50 mg/mL | 0.657 | 0.676 | 0.674 | 0.645 | 0.216 | 0.44 | 0.01 | 2.99 | −98.0 |
| 0.7% Proclin 300 | 0 mg/mL | 0.585 | 0.473 | 0.625 | 0.414 | 0.22 | 0.32 | 0.09 | 29.46 | −86.0 |
| | 5 mg/mL | 0.907 | 0.938 | 0.922 | 0.893 | 0.221 | 0.69 | 0.02 | 3.09 | −87.3 |
| | 25 mg/mL | 0.769 | 0.787 | 0.807 | 0.787 | 0.223 | 0.56 | 0.01 | 2.41 | −87.3 |
| | 50 mg/mL | 0.651 | 0.656 | 0.677 | 0.657 | 0.227 | 0.44 | 0.01 | 2.51 | −81.6 |
| | | | | | | 0.222 | | | | |

| Day 14 | | 1 | 2 | 3 | 4 | 5 | 6 | MEAN | Stdev | CV | 7 |
|---|---|---|---|---|---|---|---|---|---|---|---|
| 1.4% Proclin 300 | 0 mg/mL | 0.238 | 0.235 | 0.229 | 0.236 | 0.234 | 0.24 | 0.01 | 0.00 | 27.95 | 0.65 |
| | 5 mg/mL | 0.229 | 0.221 | 0.218 | 0.213 | 0.221 | 0.22 | 0.00 | 0.01 | −294.37 | 0.987 |
| | 25 mg/mL | 0.228 | 0.21 | 0.21 | 0.207 | 0.209 | 0.216 | −0.01 | 0.01 | −89.66 | 0.825 |
| | 50 mg/mL | 0.227 | 0.211 | 0.206 | 0.208 | 0.209 | 0.214 | −0.01 | 0.01 | −83.22 | 0.652 |
| 0.7% Proclin 300 | 0 mg/mL | 0.226 | 0.215 | 0.211 | 0.206 | 0.213 | 0.212 | −0.01 | 0.01 | −90.47 | 0.698 |
| | 5 mg/mL | 0.226 | 0.214 | 0.206 | 0.208 | 0.213 | 0.219 | −0.01 | 0.01 | −86.88 | 0.993 |
| | 25 mg/mL | 0.232 | 0.218 | 0.213 | 0.211 | 0.215 | 0.221 | 0.00 | 0.01 | −182.48 | 0.841 |
| | 50 mg/mL | 0.245 | 0.232 | 0.233 | 0.233 | 0.234 | 0.237 | 0.01 | 0.01 | 41.56 | 0.672 |
| | | | | | | | 0.222 | | | | |

| Day 14 | | 8 | 9 | 10 | 11 | 12 | MEAN | Stdev | CV | % Bias |
|---|---|---|---|---|---|---|---|---|---|---|
| 1.4% Proclin 300 | 0 mg/mL | 0.655 | 0.662 | 0.648 | 0.664 | 0.243 | 0.43 | 0.01 | 1.65 | −97.2 |
| | 5 mg/mL | 0.959 | 0.967 | 1.007 | 0.986 | 0.225 | 0.75 | 0.02 | 2.50 | −100.3 |
| | 25 mg/mL | 0.799 | 0.805 | 0.829 | 0.817 | 0.222 | 0.59 | 0.01 | 2.18 | −101.6 |
| | 50 mg/mL | 0.643 | 0.64 | 0.67 | 0.655 | 0.219 | 0.42 | 0.01 | 2.78 | −102.4 |
| 0.7% Proclin 300 | 0 mg/mL | 0.619 | 0.623 | 0.617 | 0.609 | 0.217 | 0.41 | 0.04 | 9.11 | −102.0 |
| | 5 mg/mL | 0.992 | 0.972 | 1.009 | 0.992 | 0.222 | 0.76 | 0.01 | 1.72 | −101.2 |
| | 25 mg/mL | 0.843 | 0.815 | 0.846 | 0.808 | 0.227 | 0.60 | 0.02 | 2.93 | −100.8 |
| | 50 mg/mL | 0.653 | 0.659 | 0.682 | 0.685 | 0.242 | 0.44 | 0.01 | 3.16 | −97.1 |
| | | | | | | 0.227 | | | | |

As depicted in Table 8, creatininase (commercially offered for sale by Toyobo) enzyme activity is measured against various concentrations of Proclin™ 300 (biocide) and BSA (scavenger protein) over a period of 14 days (with absorbance measurement taken at 0, 4, and 14 days) for five different aqueous solutions (represented as columns 1-5—column 6 is a blank). In addition, five replicate solutions were also tested (represented as columns 7-11—column 12 is a blank) in which such replicate solutions contain only BSA and do not include any concentrations of the Proclin™

300 biocide. As can be seen in Table 8, at day 4 and at Proclin™ 300 biocide concentrations of 0.7%, the aqueous solutions (columns 1-5) comprising 5 mg/mL, 25 mg/mL, and 50 mg/mL concentrations of BSA show increased (albeit a mild increase) absorbance of the creatininase enzyme (as compared to samples containing 0 mg/mL of BSA). At day 14, the creatininase enzyme activity remains low, but there is an increase in the absorbance for preservation fluids 1-5 as the concentration of BSA is increased from 5 mg/mL to 25 mg/mL to 50 mg/mL. However, solutions 7-11, which only contain BSA and no Proclin™ 300 biocide, show increased (or at least maintained) creatininase absorbance at days 4 and 14 (with the highest absorbance being measured at BSA concentrations of 5 mg/mL), which illustrates BSA's preservative effect on creatininase enzyme activity.

TABLE 8

Toyobo Creatininase Enzyme Absorbance with BSA and Proclin ™ 300

| Day 0 | BSA | 1 | 2 | 3 | 4 | 5 | 6 | MEAN | Stdev | CV | 7 |
|---|---|---|---|---|---|---|---|---|---|---|---|
| 1.4% Proclin 300 | 0 mg/mL | 0.582 | 0.538 | 0.549 | 0.537 | 0.536 | 0.113 | 0.43 | 0.02 | 4.54 | 0.595 |
| | 5 mg/mL | 0.592 | 0.541 | 0.531 | 0.516 | 0.526 | 0.112 | 0.42 | 0.03 | 7.06 | 0.571 |
| | 25 mg/mL | 0.547 | 0.508 | 0.496 | 0.517 | 0.523 | 0.109 | 0.40 | 0.02 | 4.77 | 0.529 |
| | 50 mg/mL | 0.52 | 0.484 | 0.471 | 0.485 | 0.491 | 0.112 | 0.37 | 0.02 | 4.90 | 0.507 |
| 0.7% Proclin 300 | 0 mg/mL | 0.497 | 0.456 | 0.477 | 0.457 | 0.465 | 0.106 | 0.35 | 0.02 | 4.86 | n/a |
| | 5 mg/mL | 0.539 | 0.503 | 0.493 | 0.494 | 0.515 | 0.107 | 0.39 | 0.02 | 4.89 | 0.749 |
| | 25 mg/mL | 0.534 | 0.505 | 0.503 | 0.52 | 0.523 | 0.106 | 0.40 | 0.01 | 3.26 | 0.529 |
| | 50 mg/mL | 0.162 | 0.122 | 0.104 | 0.17 | 0.136 | 0.187 0.119 | 0.02 | 0.03 | 138.61 | 0.973 |

| Day 0 | BSA | 8 | 9 | 10 | 11 | 12 | MEAN | Stdev | CV | % Bias |
|---|---|---|---|---|---|---|---|---|---|---|
| 1.4% Proclin 300 | 0 mg/mL | 0.557 | 0.575 | 0.546 | 0.51 | 0.107 | 0.45 | 0.03 | 7.09 | −4.8 |
| | 5 mg/mL | 0.569 | 0.573 | 0.57 | 0.582 | 0.113 | 0.47 | 0.01 | 1.12 | −9.7 |
| | 25 mg/mL | 0.508 | 0.507 | 0.518 | 0.514 | 0.106 | 0.41 | 0.01 | 2.18 | −2.6 |
| | 50 mg/mL | 0.488 | 0.464 | 0.506 | 0.524 | 0.103 | 0.39 | 0.02 | 5.81 | −5.4 |
| 0.7% Proclin 300 | 0 mg/mL | n/a | n/a | n/a | n/a | n/a | n/a | n/a | n/a | n/a |
| | 5 mg/mL | 0.71 | 0.679 | 0.724 | 0.734 | 0.101 | 0.61 | 0.03 | 4.33 | −36.5 |
| | 25 mg/mL | 0.49 | 0.506 | 0.514 | 0.499 | 0.103 | 0.40 | 0.01 | 3.70 | −1.0 |
| | 50 mg/mL | 1.685 | 1.801 | 1.683 | 1.36 | n/a 0.106 | 1.39 | 0.34 | 24.20 | −98.6 |

| Day 4 | | 1 | 2 | 3 | 4 | 5 | 6 | MEAN | Stdev | CV | 7 |
|---|---|---|---|---|---|---|---|---|---|---|---|
| 1.4% Proclin 300 | 0 mg/mL | 0.357 | 0.353 | 0.355 | 0.354 | 0.356 | 0.235 | 0.13 | 0.00 | 1.19 | 0.754 |
| | 5 mg/mL | 0.331 | 0.322 | 0.322 | 0.314 | 0.329 | 0.216 | 0.10 | 0.01 | 6.67 | 1 |
| | 25 mg/mL | 0.316 | 0.299 | 0.299 | 0.293 | 0.305 | 0.213 | 0.08 | 0.01 | 10.91 | 0.872 |
| | 50 mg/mL | 0.319 | 0.301 | 0.302 | 0.308 | 0.31 | 0.221 | 0.09 | 0.01 | 8.49 | 0.763 |
| 0.7% Proclin 300 | 0 mg/mL | 0.429 | 0.419 | 0.431 | 0.404 | 0.422 | 0.218 | 0.20 | 0.01 | 5.39 | 0.758 |
| | 5 mg/mL | 0.469 | 0.457 | 0.464 | 0.472 | 0.464 | 0.225 | 0.24 | 0.01 | 2.36 | 1.095 |
| | 25 mg/mL | 0.434 | 0.42 | 0.427 | 0.424 | 0.425 | 0.223 | 0.20 | 0.01 | 2.53 | 0.934 |
| | 50 mg/mL | 0.445 | 0.439 | 0.437 | 0.447 | 0.447 | 0.23 0.223 | 0.22 | 0.00 | 2.13 | 0.781 |

| Day 4 | | 8 | 9 | 10 | 11 | 12 | MEAN | Stdev | CV | % Bias |
|---|---|---|---|---|---|---|---|---|---|---|
| 1.4% Proclin 300 | 0 mg/mL | 0.751 | 0.74 | 0.731 | 0.713 | 0.23 | 0.51 | 0.02 | 3.24 | −74.2 |
| | 5 mg/mL | 0.988 | 0.984 | 1.036 | 1.006 | 0.224 | 0.78 | 0.02 | 2.65 | −87.0 |
| | 25 mg/mL | 0.841 | 0.872 | 0.896 | 0.856 | 0.217 | 0.64 | 0.02 | 3.20 | −87.6 |
| | 50 mg/mL | 0.762 | 0.756 | 0.807 | 0.763 | 0.222 | 0.54 | 0.02 | 3.81 | −84.3 |
| 0.7% Proclin 300 | 0 mg/mL | 0.736 | 0.747 | 0.73 | 0.746 | 0.224 | 0.52 | 0.01 | 2.09 | −61.7 |
| | 5 mg/mL | 1.072 | 1.093 | 1.13 | 1.104 | 0.222 | 0.87 | 0.02 | 2.41 | −72.2 |
| | 25 mg/mL | 0.899 | 0.904 | 0.92 | 0.891 | 0.227 | 0.68 | 0.02 | 2.52 | −70.3 |
| | 50 mg/mL | 0.761 | 0.765 | 0.817 | 0.784 | 0.236 0.225 | 0.56 | 0.02 | 3.98 | −60.4 |

| Day 14 | | 1 | 2 | 3 | 4 | 5 | 6 | MEAN | Stdev | CV | 7 |
|---|---|---|---|---|---|---|---|---|---|---|---|
| 1.4% Proclin 300 | 0 mg/mL | 0.24 | 0.231 | 0.227 | 0.229 | 0.231 | 0.231 | 0.01 | 0.00 | 36.62 | 0.734 |
| | 5 mg/mL | 0.221 | 0.212 | 0.212 | 0.208 | 0.212 | 0.214 | −0.01 | 0.00 | −95.92 | 1.137 |
| | 25 mg/mL | 0.22 | 0.207 | 0.207 | 0.203 | 0.204 | 0.211 | −0.01 | 0.01 | −69.73 | 0.935 |
| | 50 mg/mL | 0.22 | 0.209 | 0.204 | 0.202 | 0.203 | 0.211 | −0.01 | 0.01 | −71.50 | 0.78 |
| 0.7% Proclin 300 | 0 mg/mL | 0.228 | 0.217 | 0.217 | 0.216 | 0.216 | 0.21 | 0.00 | 0.01 | 645.90 | 0.705 |
| | 5 mg/mL | 0.228 | 0.218 | 0.214 | 0.216 | 0.22 | 0.218 | 0.00 | 0.01 | 450.31 | 1.14 |
| | 25 mg/mL | 0.235 | 0.225 | 0.224 | 0.226 | 0.232 | 0.221 | 0.01 | 0.00 | 46.41 | 0.937 |
| | 50 mg/mL | 0.299 | 0.295 | 0.29 | 0.292 | 0.297 | 0.228 0.218 | 0.08 | 0.00 | 4.76 | 0.782 |

| Day 14 | | 8 | 9 | 10 | 11 | 12 | MEAN | Stdev | CV | % Bias |
|---|---|---|---|---|---|---|---|---|---|---|
| 1.4% Proclin 300 | 0 mg/mL | 0.719 | 0.726 | 0.731 | 0.701 | 0.231 | 0.50 | 0.01 | 2.62 | −97.3 |
| | 5 mg/mL | 1.102 | 1.097 | 1.154 | 1.116 | 0.219 | 0.90 | 0.02 | 2.67 | −100.6 |
| | 25 mg/mL | 0.921 | 0.928 | 0.947 | 0.932 | 0.215 | 0.71 | 0.01 | 1.35 | −101.4 |
| | 50 mg/mL | 0.776 | 0.779 | 0.806 | 0.797 | 0.215 | 0.57 | 0.01 | 2.32 | −101.8 |
| 0.7% | 0 mg/mL | 0.721 | 0.727 | 0.73 | 0.719 | 0.216 | 0.50 | 0.01 | 1.94 | −99.8 |

TABLE 8-continued

Toyobo Creatininase Enzyme Absorbance with BSA and Proclin™ 300

| Proclin 300 | 5 mg/mL | 1.136 | 1.128 | 1.161 | 1.141 | 0.219 | 0.92 | 0.01 | 1.33 | −99.9 |
|---|---|---|---|---|---|---|---|---|---|---|
| | 25 mg/mL | 0.937 | 0.925 | 0.941 | 0.925 | 0.224 | 0.71 | 0.01 | 1.05 | −98.5 |
| | 50 mg/mL | 0.094 | 1.493 | 0.816 | 0.81 | 0.231 | 0.58 | 0.49 | 85.64 | −86.7 |
| | | | | | | 0.221 | | | | |

Non-Limiting Examples of the Inventive Concept(S)

An improved analyte detection sensor of a blood gas, electrolyte, and/or metabolite instrument, comprising: a substrate, the substrate comprising a top surface and a bottom surface; an enzyme layer, the enzyme layer comprising at least one enzyme, wherein the enzyme layer is disposed on the top surface of the substrate; a scavenger protein layer, the scavenger protein layer comprising at least one scavenger protein having at least one free sulfhydryl functional group, wherein the scavenger protein layer is disposed on the top surface of the substrate such that the scavenger protein layer substantially covers an entirety of the enzyme layer; at least one electrode, wherein the at least one electrode is disposed on the top surface of the substrate such that the at least one electrode is substantially covered by the enzyme layer; and a sensor membrane cover, the sensor membrane being disposed over the scavenger protein layer.

The improved analyte detection sensor, wherein the at least one analyte detection sensor comprises a creatinine detection sensor, further wherein the at least one enzyme is selected from the group consisting of creatininase, creatinase, sarcosine oxidase, and combination thereof.

The improved analyte detection sensor, wherein the scavenger protein layer comprises an aqueous layer upon being reconstituted with a buffer or wash solution.

The improved analyte detection sensor, wherein the at least one scavenger protein of the scavenger protein layer is selected from the group consisting of bovine serum albumin, thioredoxin, urease, glutathione, cadystin, phytochelatin, homoglutathione, homophytochelatin, desGly peptide, desglycine phytochelatin, hydroxymethyl-glutathione, hydroxymethyl-phytochelatin, and combinations thereof.

The improved analyte detection sensor, wherein the at least one scavenger protein of the scavenger protein layer consists of bovine serum albumin comprising a concentration of from about 0.1 milligram per milliliter to about 50 milligrams per milliliter.

The improved analyte detection sensor, wherein the at least one scavenger protein of the scavenger protein layer comprises from about 1 to about 20 free sulfhydryl functional groups.

The improved analyte detection sensor, wherein the analyte detection sensor array is contained within a housing.

The improved analyte detection sensor, wherein the housing comprises a cartridge for use in a blood gas, electrolyte, and/or metabolite instrument.

A method for preventing the inactivation of at least one analyte detection sensor of a blood gas, electrolyte, and/or metabolite instrument, the method comprising the steps of: introducing at least one aqueous biocide such that the at least one aqueous biocide is in fluid communication with at least one analyte detection sensor, the at least analyte detection sensor comprising: a substrate, the substrate comprising a top surface and a bottom surface; an enzyme layer, the enzyme layer comprising at least one enzyme, wherein the enzyme layer is disposed on the top surface of the substrate; a scavenger protein layer, the scavenger protein layer comprising at least one scavenger protein having at least one free sulfhydryl functional group, wherein the scavenger protein layer is disposed on the top surface of the substrate such that the scavenger protein layer substantially covers an entirety of the enzyme layer; at least one electrode, wherein the at least one electrode is disposed on the top surface of the substrate such that the at least one electrode is substantially covered by the enzyme layer; and a sensor membrane cover, the sensor membrane being disposed over the scavenger protein layer; reacting the at least one aqueous biocide and the at least one scavenger protein of the scavenger protein layer such that the at least one aqueous biocide associates with the at least one free sulfhydryl functional group of the at least one scavenger protein of the scavenger protein layer to thereby form a complexed biocide; and contacting the at least one analyte detection sensor with the complexed biocide fluid, such that the complexed biocide prevents inactivation of the at least one enzyme of the enzyme layer.

The method, wherein the at least one analyte detection sensor comprises a creatinine detection sensor.

The method, wherein the at least on enzyme is selected from the group consisting of creatininase, creatinase, sarcosine oxidase, and combinations thereof.

The method, wherein the at least one aqueous biocide is selected from the group consisting methylisothiazolinone, Proclin™ 300, and combinations thereof.

The method, wherein the methylisothiazolinone comprises a concentration of from about 1 part per million to about 150 parts per million.

The method, wherein the Proclin™ 300 comprises a concentration of from about 0.1% to about 2.0%.

The method, wherein the scavenger protein layer comprises an aqueous layer upon being reconstituted by a buffer or wash solution.

The method, wherein the at least scavenger protein is selected from the group consisting of bovine albumin serum, thioredoxin, urease, glutathione, cadystin, phytochelatin, homoglutathione, homophytochelatin, desGly peptide, desglycine phytochelatin, hydroxymethyl-glutathione, hydroxymethyl-phytochelatin, and combination thereof.

The method, wherein the at least one scavenger protein consists of bovine serum albumin comprising a concentration of from about 0.1 milligram per milliliter to about 50 milligrams per milliliter of a total volume of the preservation fluid.

The method, wherein the at least one scavenger protein comprises from about 1 to about 20 free sulfhydryl functional groups.

The method, wherein the analyte detection sensor array is contained within a housing.

The method, wherein the housing comprises a cartridge for use in a blood gas, electrolyte, and/or metabolite instrument.

An improved analyte detection sensor of a blood gas, electrolyte, and/or metabolite instrument, comprising: a substrate, the substrate comprising a top surface and a bottom surface; a reaction cavity, the reaction cavity having a first side, a second side, a third side, and fourth side, the reaction cavity being located between the top surface and the bottom surface of the substrate with the first side, second side, third side, and fourth side defining an opening of the reaction cavity substantially near the top surface of the substrate; an enzyme layer, the enzyme layer comprising at least one enzyme, wherein the enzyme layer is disposed substantially within the reaction cavity; a scavenger protein layer, the scavenger protein layer comprising at least one scavenger protein having at least one free sulfhydryl functional group, wherein the scavenger protein layer is disposed on the top surface of the substrate such that the scavenger protein layer substantially covers the opening of the reaction cavity; at least one electrode, wherein the at least one electrode is disposed within the reaction cavity below the enzyme layer; and a sensor membrane cover, the sensor membrane being disposed over the scavenger protein layer.

Thus, in accordance with the presently disclosed and claimed inventive concept(s), there have been provided devices, kits, and methods for detecting at least one analyte present in a patient's low-volume liquid test sample. As described herein, the presently disclosed and claimed inventive concept(s) relate to embodiments of an improved analyte detection sensor comprising at least one scavenger protein, as well as kits and methods of inhibiting the inactivation of at least one enzyme of the improved analyte detection sensor. Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed and claimed inventive concept(s).

What is claimed is:

1. An improved analyte detection sensor of a blood gas, electrolyte, and/or metabolite instrument, wherein the improved analyte detection sensor comprises a creatinine detection sensor, the improved analyte detection sensor comprising:
    a substrate, the substrate comprising a top surface and a bottom surface;
    at least one electrode disposed on the top surface of the substrate;
    an enzyme layer disposed on the top surface of the substrate such that the at least one electrode is substantially covered by the enzyme layer, wherein the enzyme layer comprises creatininase, creatinase, and sarcosine oxidase;
    a scavenger protein or peptide layer, the scavenger protein or peptide layer consisting essentially of at least one scavenger protein or peptide having at least one free sulfhydryl functional group, wherein the scavenger protein or peptide layer is disposed on the top surface of the substrate such that the scavenger protein or peptide layer substantially covers an entirety of the enzyme layer, and wherein the at least one scavenger protein or peptide is selected from the group consisting of bovine serum albumin, thioredoxin, urease, glutathione, cadystin, phytochelatin, homoglutathione, homophytochelatin, desglycine peptide, desglycine phytochelatin, hydroxymethyl-glutathione, hydroxymethyl-phytochelatin, and combinations thereof; and
    a sensor membrane cover, the sensor membrane cover being disposed over the scavenger protein or peptide layer such that the sensor membrane cover substantially covers an entirety of the scavenger protein or peptide layer;
    wherein the analyte detection sensor is contained within a housing; and
    wherein the analyte detection sensor has a functional life of at least about 14 days when in fluid communication with at least one aqueous biocide.

2. The improved analyte detection sensor of claim 1, wherein the scavenger protein or peptide layer is in the form of an aqueous layer upon being reconstituted with a buffer or wash solution.

3. The improved analyte detection sensor of claim 1, wherein the at least one scavenger protein or peptide of the scavenger protein or peptide layer consists of bovine serum albumin having a concentration of from about 0.1 milligram per milliliter to about 50 milligrams per milliliter.

4. The improved analyte detection sensor of claim 1, wherein the at least one scavenger protein or peptide of the scavenger protein or peptide layer has 1 to about 20 free sulfhydryl functional groups.

5. The improved analyte detection sensor of claim 1, wherein the housing comprises a cartridge for use in a blood gas, electrolyte, and/or metabolite instrument.

6. A method for preventing the inactivation of at least one analyte detection sensor of a blood gas, electrolyte, and/or metabolite instrument, wherein the at least one analyte detection sensor comprises a creatinine detection sensor, the method comprising the steps of:
    introducing at least one aqueous biocide such that the at least one aqueous biocide is in fluid communication with at least one analyte detection sensor, the at least analyte detection sensor comprising:
        a substrate, the substrate comprising a top surface and a bottom surface;
        at least one electrode disposed on the top surface of the substrate;
        an enzyme layer disposed on the top surface of the substrate such that the at least one electrode is substantially covered by the enzyme layer, wherein the enzyme layer comprises creatininase, creatinase, and sarcosine oxidase;
        a scavenger protein or peptide layer, the scavenger protein or peptide layer consisting essentially of at least one scavenger protein or peptide having at least one free sulfhydryl functional group, wherein the scavenger protein or peptide layer is disposed on the top surface of the substrate such that the scavenger protein or peptide layer substantially covers an entirety of the enzyme layer, and wherein the at least one scavenger protein or peptide selected from the group consisting of bovine serum albumin, thioredoxin, urease, glutathione, cadystin, phytochelatin, homoglutathione, homophytochelatin, desglycine peptide, desglycine phytochelatin, hydroxymethyl-glutathione, hydroxymethyl-phytochelatin, and combinations thereof; and
        a sensor membrane cover, the sensor membrane cover being disposed over the scavenger protein or peptide layer such that the sensor membrane cover substantially covers an entirety of the scavenger protein or peptide layer;
    reacting the at least one aqueous biocide and the at least one scavenger protein or peptide of the scavenger protein or peptide layer such that the at least one aqueous biocide associates with the at least one free sulfhydryl functional group of the at least one scavenger protein or peptide of the scavenger protein or peptide layer to thereby form a complexed biocide; and contacting the at least one analyte detection sensor with the complexed biocide fluid, such that the complexed biocide prevents inactivation of the at least one enzyme of the enzyme layer; and wherein the at least one analyte detection sensor comprises a creatinine detection sensor.

7. The method of claim 6, wherein the at least one aqueous biocide is selected from the group consisting methylisothiazolinone, 5 chloro-2-methyl-4-isothiazolin-3-one ("CMIT"), MIT, proprietary glycol, modified alkyl carboxylate, and combinations thereof.

8. The method of claim 7, wherein the methylisothiazolinone comprises a concentration of from about 1 part per million to about 150 parts per million.

9. The method of claim 7, wherein the aqueous biocide comprises a combination of CMIT, MIT, proprietary glycol, and modified alkyl carboxylate, and wherein the aqueous biocide comprises a concentration of from about 0.1% to about 2.0%.

10. The method of claim 6, wherein the scavenger protein or peptide layer is in the form of an aqueous layer upon being reconstituted by a buffer or wash solution.

11. The method of claim 6, wherein the at least one scavenger protein or peptide consists of bovine serum albumin having a concentration of from about 0.1 milligram per milliliter to about 50 milligrams per milliliter of a total volume of the preservation fluid.

12. The method of claim 6, wherein the at least one scavenger protein or peptide has 1 to about 20 free sulfhydryl functional groups.

13. An improved analyte detection sensor of a blood gas, electrolyte, and/or metabolite instrument, wherein the improved analyte detection sensor comprises a creatinine detection sensor, the improved analyte detection sensor comprising:

a substrate, the substrate comprising a top surface and a bottom surface;

a reaction cavity, the reaction cavity having a first side, a second side, a third side, and fourth side, the reaction cavity being located between the top surface and the bottom surface of the substrate with the first side, second side, third side, and fourth side defining an opening of the reaction cavity substantially near the top surface of the substrate;

at least one electrode disposed within the reaction cavity;

an enzyme layer disposed substantially within the reaction cavity and on the at least one electrode, and wherein the enzyme layer comprises creatininase, creatinase, and sarcosine oxidase;

a scavenger protein or peptide layer, the scavenger protein or peptide layer consisting essentially of at least one scavenger protein or peptide having at least one free sulfhydryl functional group, wherein the scavenger protein or peptide layer is disposed on the top surface of the substrate such that the scavenger protein or peptide layer substantially covers the opening of the reaction cavity, and wherein the at least one scavenger protein or peptide is selected from the group consisting of bovine serum albumin, thioredoxin, urease, glutathione, cadystin, phytochelatin, homoglutathione, homophytochelatin, desglycine peptide, desglycine phytochelatin, hydroxymethyl-glutathione, hydroxymethyl-phytochelatin, and combinations thereof; and a sensor membrane cover, the sensor membrane cover being disposed over the scavenger protein or peptide layer such that the sensor membrane cover substantially covers an entirety of the scavenger protein or peptide layer; and wherein the at least one analyte detection sensor has a functional life of at least about 14 days when in fluid communication with at least one aqueous biocide.

14. The improved analyte detection sensor of claim 1, wherein the at least one scavenger protein consists of bovine serum albumin.

15. The improved analyte detection sensor of claim 1, wherein the at least one scavenger protein consists of at least one of thioredoxin or urease.

16. The method of claim 6, wherein the at least one scavenger protein consists of bovine serum albumin.

17. The method of claim 6, wherein the at least one scavenger protein consists of at least one of thioredoxin or urease.

18. The improved analyte detection sensor of claim 13, wherein the at least one scavenger protein consists of bovine serum albumin.

19. The improved analyte detection sensor of claim 13, wherein the at least one scavenger protein consists of at least one of thioredoxin or urease.

* * * * *